(12) United States Patent
Jermy et al.

(10) Patent No.: US 11,717,489 B2
(45) Date of Patent: *Aug. 8, 2023

(54) CHITOSAN-COATED PLATINUM FERRITE-SILICA SPINEL NANOCOMPOSITE

(71) Applicant: Imam Abdulrahman Bin Faisal University, Dammam (SA)

(72) Inventors: B. Rabindran Jermy, Dammam (SA); Vijaya Ravinayagam, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 201 days.

This patent is subject to a terminal disclaimer.

(21) Appl. No.: 17/101,614

(22) Filed: Nov. 23, 2020

(65) Prior Publication Data
US 2022/0160643 A1     May 26, 2022

(51) Int. Cl.
| | |
|---|---|
| A61K 9/51 | (2006.01) |
| A61K 33/243 | (2019.01) |
| A61K 9/50 | (2006.01) |
| A61K 9/16 | (2006.01) |
| A61P 35/00 | (2006.01) |

(52) U.S. Cl.
CPC .......... *A61K 9/5115* (2013.01); *A61K 9/1611* (2013.01); *A61K 9/1676* (2013.01); *A61K 9/1682* (2013.01); *A61K 9/5036* (2013.01); *A61K 9/5089* (2013.01); *A61K 33/243* (2019.01); *A61P 35/00* (2018.01)

(58) Field of Classification Search
None
See application file for complete search history.

(56) References Cited

U.S. PATENT DOCUMENTS

| | | | |
|---|---|---|---|
| 9,782,342 B2 | 10/2017 | Asmatulu et al. | |
| 2020/0338122 A1* | 10/2020 | Jermy | A61P 35/00 |
| 2022/0072034 A1* | 3/2022 | Jermy | A61K 33/243 |

FOREIGN PATENT DOCUMENTS

| | | |
|---|---|---|
| CN | 102295313 B | 3/2015 |
| CN | 105963717 A | 9/2016 |
| CN | 104225599 B | 5/2017 |
| IN | 201641038101 A | 3/2018 |

OTHER PUBLICATIONS

Hu et al. (Chem Asian J. 2014, 9, 319-327).*
Zhang et al. (Chemosphere 68 (2007) 1058-1066),.*
Kong et al. (8th World Congress Nanocomposites 2008).*
Rejeeth et al. (Cancer Nano (2013) 4:127-136).*
Lopez-Ramon (Journal of Colloid and Interface Science 511 (2018) 193-202).*
Buchman et al. (ACS Sustainable Chem. Eng. 2019, 7, 19649-19659),.*
Abstractor Doctoral Thesis, Claesson, E.M., Magnetic Core-Shell Silica Particles (2007).*
Choi et al. (Journal of Photochemistry & Photobiology, B: Biology 235 (2022)).*
Juan WU, et al., "Synthesis and characterization of mesoporous magnetic nanocomposites wrapped with chitosan gatekeepers for pH-sensitive controlled release of doxorubicin", Materials Science and Engineering: C, vol. 70, Part 1, Jan. 1, 2017, pp. 132-140 (Abstract only).
Wararat Montha, et al., "Synthesis of doxorubicin-PLGA loaded chitosan stabilized (Mn, Zn)Fe₂O₄ nanoparticles: Biological activity and pH-responsive drug release", Materials Science and Engineering: C, vol. 59, Feb. 1, 2016, pp. 235-240 (Abstract only).
Maryam Radmansouri, et al., "Doxorubicin hydrochloride—Loaded electrospun chitosan/cobalt ferrite/titanium oxide nanofibers for hyperthermic tumor cell treatment and controlled drug release", International Journal of Biological Macromolecules, vol. 116, Sep. 2018, pp. 378-384 (Abstract only).
Saeid Ramezani, et al., "Synthesis and characterization of chitosan-coating of NiFe₂O₄ nannoparticles for biomedical applications", Proceedings of theh 6th International Conference on Nanostructures (ICNS6), Mar. 7-10, 2016, 3 pages.

* cited by examiner

Primary Examiner — Patricia Duffy
Assistant Examiner — Garen Gotfredson
(74) Attorney, Agent, or Firm — Oblon, McClelland, Maier & Neustadt, L.L.P.

(57) ABSTRACT

Chitosan can be coated, e.g., in 0.06 or 0.6 wt. %, over spherical silica, e.g., HYPS, loaded with spinel ferrites of theoretical formula MFe₂O₄, wherein M is Ni, Cu, Co, and/or Mn, e.g., at 30 wt. %, and cisplatin. Chitosan can be fabricated over Pt or cisplatin) bound CuFe₂O₄-HYPS and CuFe₂O₄-HYPS followed by Pt loading. Cisplatin and Pt—CuFe₂O₄-HYPS-chitosan at 0.025 to 0.5 mg/mL exhibit cytotoxicity against human breast cancer cell line (MCF-7) and human embryonic kidney cells (HEK293), relative to Pt—CuFe₂O₄-HYPS, with Pt—CuFe₂O₄-HYPS-chitosan, showing non-significant anti-cancer effects due to mediated Pt release. Pt—CuFe₂O₄/HYPS and CuFe₂O₄-HYPS-chitosan-Pt reduced cell viability using a different dose effect. Cisplatin in certain composites was less cytotoxic to HEK293 than MCF7, making the a targeted drug delivery system. Inventive composites may improve multifunctional theranostic applications involving pH stimuli, temperature-based drug release, and diagnosis based treatment such as hyperthermia.

11 Claims, 28 Drawing Sheets

CHITOSAN-COATED PLATINUM FERRITE-SILICA SPINEL NANOCOMPOSITE

BACKGROUND OF THE INVENTION

Field of the Invention

The present disclosure relates to composites capable of controlled release of therapeutic agents, such as anticancer agents including platinum-containing drugs, e.g., cisplatin, carboxyplatin, oxaliplatin, etc., particularly relating to magnetic composites, such as ferrite-based materials, preferably doped with further metals, e.g., Cu, Ni, Mo, and/or Mn, and hosted by silica carrier, and methods of making and using such composites.

Description of the Related Art

Cancer is presently one of the most widely suffered and feared diseases in the world, causing millions of annual deaths. According to cancer statistics from 2018, the number of new cancer cases in the U.S. was estimated to be 1,735,350 and related deaths were estimated to be 609,640. There is an expectation that cancer cases will increase to about 24 million worldwide by 2035.

Nanotherapeutics based on chitosan-bound silica, carbon nanotubes, halloysite (aluminosilicate clay mineral with the empirical formula $Al_2Si_2O_5(OH)_4$), and graphene oxide are emerging as versatile tools in targeted drug delivery applications. The medicinal use of nanoparticles has evolved from the monotonous role as a drug delivery system, e.g., as a carrier, to multifunctional roles including labelling, drug transport, gene transport, detection of pathogens and/or proteins, as RNA and/or DNA probe, optical imaging enhancer, tissue design, bio molecule isolation, cell isolation, and tumor antagonist and/or agonist.

Nanotechnology research and nanoscale biomedical technology have triggered a renewed interest in utilizing such materials, including spinel ferrites, for therapeutic and diagnostic applications. Nanosized carriers can be effective diagnostic probes for in vitro and in vivo cellular and molecular imaging. The role of a diagnostic nanoscale silica drug carrier can include responding to an external (electromagnetic) field and thereby assisting the bioimaging, as a magnetic targeting agent to carry a drug, and for drug delivery. For example, magnetic "nanosilicas" may have commercial potential as cancer targeting drugs. Some nanosilicas have shown success in animal studies and in clinical trials.

Cobalt ferrite nanoparticles of 20 nm average particle size have been reported to deliver 90% doxorubicin in 6 hours at 44° C. using hyperthermia, whereby the saturation magnetization was reported to be about 54 emu/g. Manganese ferrite nanoparticles bound with chitosan and polyethylene glycol polymers have been reported to encapsulate a high percentage of methotrexate (92.8%). Magnetically active manganese ferrite nanoparticles with an emu/g of 19.7 showed pH influenced release under acidic pH conditions. Nickel ferrite nanoparticles have been studied for cytotoxicity in HepG2 and MCF-7 cell lines. Real-time PCR studies have shown an apoptotic effect caused mainly by the alteration in mRNA genes.

Copper ferrite prepared by sol-gel techniques have been shown to generate tetragonal crystalline $CuFe_2O_4$ nanoparticles. Calcination effect studies have shown that $CuFe_2O_4$ nanoparticles exhibit magnetic values of up to 30 emu/g at a calcination temperature of 300° C. An increase in biocompatibility but decrease of magnetic saturation value of about 6 emu/g was observed with a similar silica nanocomposite. Though such modifications can be effective, the targeted diffusion and bioavailability of such nanoscale formulations are often low, e.g., 5 to 10%. In addition, the nanoformulations are still marred by issues like toxicity at high dosage levels, passivation due to multiple inorganics, and low pH sensitivity. For instance, the presence of nickel in a spinel system, e.g., 200 microgram per mL, has been shown to increase toxicity and induce oxidative stress.

In order to reduce known toxicity problems, several types of biocompatible polymers have been investigated. The presence of a polymer coating over manganese ferrite has been reported to control the release of at least one drug, while showing almost no nanoparticle based cytotoxicity. A HepG2 cell line study revealed that chitosan bound silica nanoparticles with folic acid conjugation along with glutathione over zeolite exhibit anticancer activity. An ellipsoid type of zeolite ZSM-5 with a hollow core was found to exhibit high doxorubicin adsorption capacity, i.e., around 95.8%. Chitosan wrapping over a nanoscale ZSM-5-doxorubicin formulation showed biocompatibility and pH-sensitive doxorubicin release towards MG63 cells. Chitosan capping over functionalized spherical mesoporous silica, including functionalized silica, chitosan, folic acid, and a drug, has been reported for anastrozole delivery, which, compared to conventionally delivered anastrozole, showed about a four-fold higher antitumor activity.

A layer-by-layer coating with oppositely charged polymer complexes including chitosan and κ-carrageenan, over cubically structured KIT-6 and KIL-2 silicas has been reported to exert a sustained release of curcumin with an antiproliferative effect. Thin films of chitosan coated via disulfide linkages over mesoporous silica were reported to exhibit dual stimuli responses, i.e., to pH and glutathione, for doxorubicin release.

The preparation of $NiFe_2O_4$ using a combustion technique followed by polyethylene glycol coating was reported to improve biocompatibility. The formation of an agglomerated foam-like morphology was observed for $NiFe_2O_4$ with a saturation magnetization value of 35 emu/g. A $NiFe_2O_4$ nanoparticle composite involving polypyrrole-chitosan prepared by an electrochemical polymerization technique has likewise been reported.

However, cisplatin release from a chitosan coated or wrapped HYPS over spinel ferrite impregnated monodispersed spherical silica wrapped with chitosan, and its in vitro study, are lacking.

CN 104225599 B by Li et al. (Li) discloses a nanometer drug carrier, asymmetric magnetic mesoporous silica rod supporting chemotherapeutic and gene drugs, and its application in tumor diagnosis and treatment. Li's material is prepared from spherical magnetic ferrite nanoparticles and ethyl orthosilicate via a sol-gel method, surface functionalization, successive loading with a chemotherapeutic drug, coating by a cationic polymer, and loading with a gene drug. Li's chemotherapeutic drug is connected to the silica rod by functionalization of the mesoporous surface, and the silica rod has pH-responsive drug release, and the gene is electrostatically adsorbed. Li's material when injected into a living body, exhibits passive targeting, gene guidance, pH-responsive drug release, and in-vitro magnetic targeting. Li's material is rod shaped, with a length of 100 to 1000 nm, a width of 50 to 200 nm, a specific surface area of 500 to 1000 m$^2$/g, and a mesoporous pore diameter of 2 to 20 nm. Li's material contains no Ni, Cu, Co, or Mn and does not contain cisplatin.

CN 105963717 A by Liu et al. (Liu) discloses a composite nano-drug for integrated tumor diagnosis and treatment and its preparation. Liu's carrier may host a chemotherapy drug, a photodynamic drug, and shRNA plasmids capable of reversing multidrug-resistant MDR1 genes of tumor cells. Liu's carrier is a magnetic nano-sphere with precious metal nano-particles, e.g., Au or Ag, arranged on the surface of a mesoporous silica core, surface-modified with amino groups as a shell, and a pH sensitive polyelectrolyte layer on the surface of the core-shell structure. Liu uses its composite for early diagnosis of tumors, image mediation, and real-time treatment monitoring. Liu's magnetic nanosphere may comprise Ni, Co, Fe, $Fe_3O_4$, $\gamma$-$Fe_2O_3$, Ni—$Fe_3O_4$, or $CoFe_3O_4$, however, Liu requires Au or Ag.

U.S. Pat. No. 9,782,342 to Asmatulu et al. (Asmatulu) discloses a composite magnetic nanoparticle drug delivery system for targeted, controlled-release chemotherapies for cancerous tumors and inflammatory diseases. Asmatulu's material has a biocompatible, biodegradable polymer, a magnetic nanoparticle, the biological targeting agent human serum albumin, and a therapeutic pharmaceutical composition. Asmatulu describes using an externally applied magnetic field and the biological targeting agent to draw the magnetic nanoparticles to affected areas, while polymer degradation provides controlled time release delivery of the pharmaceutical agent. Asmatulu mentions $CoFe_3O_4$, chitosan, and cisplatin, but does not specifically combine these nano components, preferring polylactides.

IN 201641038101 A by Meera et al. (Meera) discloses magnetically targeted drug delivery (MTD) using iron oxide nano particles ($Fe_2O_3$/$Fe_3O_4$), coated with polymer, followed by drug encapsulation, and magnetically directed delivery to target sites. Meera uses $CaFe_2CX_i$ nano particles (CFNP), which is super paramagnetic, over simple $Fe_3O_4$ nanoparticles, coated by chitosan. Meera mentions curcumin, paclitaxel, doxorubicin, bleomycin, and non-conventional drugs, in-vitro drug delivery, and apoptosis for various cancer cell lines, e.g., MCF-5, M19-MEL, WIDR, A498, EVSA-T, H226, IGROV, for lung, breast, and skin cancer. Meera describes a hydrophobic modification of chitosan with vanillin, naphthalene acetic acid, phendione, benzimidazole, and tyrosine, and requires a calcium ferrite.

WO 2009/086824 A2 by Waldoerfner et al. (Waldoerfner), further published, inter alia, as CN 102295313, U.S. Pat. Nos. 9,814,677, and 8,771,699, discloses producing biocompatible magnetic nano-particles with a high SAR-values, which produce a large amount of heat when exposed to an alternating magnetic field. The produced heat can be used for therapeutic purposes, in particular for combating cancer, among other uses. Waldoerfner's material has an iron-comprising core and a silica shell, but does not employ metal additives with the iron.

Mater. Sci. Eng. C 2017, 70(1), 132-140 by Wu et al. (Wu) discloses multifunctional nanocarriers based on a $Fe_3O_4$ nanoparticle core and mesoporous silica shell (m$SiO_2$) for controlled drug release through magnetic targeting and pH-sensitive performances. Wu's $Fe_3O_4$@m$SiO_2$ nanocarriers were 63 nm in average size and responded to magnets, loading (29.3%) and releasing (86.1% within 48 hours at pH 4.0) doxorubicin via electrostatic interactions. Wu uses chitosan to coat the $Fe_3O_4$@m$SiO_2$-DOX as the blocking agent to inhibit premature drug release, and the final material was pH-sensitive. Wu's chitosan-coated doxorubicin-loaded $Fe_3O_4$@m$SiO_2$ had anti-tumor activity, while the carriers were non-toxic. Wu does not use platinum-containing therapeutics, nor do Wu's carriers contain Cu, Co, Mn, and/or Ni.

Mater. Sci. Eng. C 2016, 59, 235-240 by Montha et al. (Montha) discloses $Mn_{1-x}Zn_xFe_2O_4$ ((Mn, Zn) ferrite) magnetic nanoparticles (MNPs) of 25 nm radius, coated with around 50 nm of poly(lactic-co-glycolic acid) (PLGA) and chitosan, as platforms for drug delivery of doxorubicin. Montha reports that $Mn_{0.9}Zn_{0.1}Fe_2O_4$ MNPs exhibit superparamagnetic behavior with large saturation magnetization. Montha's doxorubicin-PLGA@chitosan@$Mn_{0.9}Zn_{0.1}Fe_2O_4$ shows lower toxicity against HeLa cells using doxorubicin only for concentrations lower than 125 μg/mL, but the greater toxicity at 250 μm/mL. Montha does not describe platinum-based anticancer drugs, and requires a complicated coating as well as zinc.

Int. J. Bio. Macromol. 2018, 116, 378-384 by Radmansouri et al. (Radmansouri) discloses doxorubicin HCl-loaded electrospun chitosan/cobalt ferrite/titanium oxide nanofibers for hyperthermia and chemotherapy against melanoma cancer B16F10 cell lines. Radmansouri's $TiO_2$ nanoparticles were mixed with cobalt ferrite to control the temperature rise. The fastest release of doxorubicin from Radmansouri's magnetic nanofibers was at acidic pH by alternating of magnetic field. Radmansouri's material is in the shape of fibers and requires $TiO_2$, and Radmansouri does not describe platinum-containing drugs.

The presentation entitled "Synthesis and characterization of chitosan-coating of $NiFe_2O_4$ nanoparticles for biomedical applications," published in the Proc. 6$^{th}$ Int. Conf. Nanostructures, from Mar. 7-10, 2016, in Kish, Iran, by Ramezani et al. (Ramezani) describes nickel ferrite nanoparticle, a soft magnetic material, as a catalyst or in biomedical processes. Ramezani's $NiFe_2O_4$ nanoparticles are made by co-precipitation and calcined, then dispersed in water with chitosan, thereby bonding chitosan to the nanoparticle surface. Ramezani's particles were sized 15 to 40 nm in a circular shape. Ramezani reports its coated nickel ferrite nanoparticle to be better than pure Ni ferrite nanoparticles or Co ferrite, but Ramezani does not use a carrier, nor a platinum-comprising drug.

In light of the above, a need remains for medicinal carrier nanocomposites and methods of administration, particularly for platinum-comprising and/or anticancer pharmaceuticals, such as cisplatin, carboplatin, and/or oxaliplatin, and particularly comprising biodegradable and biocompatible coatings, particularly of chitosan, as well as methods of making such nanocomposites.

SUMMARY OF THE INVENTION

Aspects of the invention provide compositions comprising: a spherical HYPS silica; a metal ferrite, $MFe_2O_4$, on an outer surface of the silica, M being Ni, Cu, Co, and/or Mn, and M being present in 15 to 45 wt. %, based on total metal ferrite weight, the silica and the metal ferrite forming at least 75 wt. % of a carrier, based on total carrier weight; a coating comprising at least 75 wt. %, based on total coating weight, of chitosan, the coating contacting the carrier on an inner surface and exposed to outside environment on an outer surface; and a platinum-containing anticancer drug, disposed within and/or on the carrier and/or the coating. Such compositions may be modified in any permutation by the features described herein, particularly the following.

The composition may be in particle form, having an irregular spheroid morphology.

The M may comprise Cu. The M may comprise at least 50 wt. %, relative to all non-ferrous metals in the metal-ferrite, of Cu.

The platinum-containing anticancer drug may comprise cisplatin, carboplatin, or oxaliplatin. The platinum-containing anticancer drug may comprise at least 75 wt. % cisplatin, relative to total platinum-containing anticancer drug weight. The platinum-containing anticancer drug may be present, in mmol per gram of the support, in a range of from 0.05 to 0.25.

The silica may have an average diameter of from 50 to 100 nm, and/or a distribution of the silica may be monomodal.

The metal ferrite may have an average particle size in a range of from 4 to 15 nm. The metal ferrite may be present in the carrier, relative to the total carrier weight, in a weight percentage of from 15 to 40 wt. %.

The chitosan in the coating may have a Mw in a range of from 30 to 250 kDa. The coating may constitute no more than 20 wt. % of total composition weight. At least 25 wt. % of the platinum-containing anticancer drug may be present in the coating.

The carrier may comprise at least 95 wt. % of the metal ferrite and the silica, based on the total carrier weight, and/or the carrier may have a pore volume in a range of from 0.15 to 0.25 $cm^3/g$. The carrier may have a saturation magnetization in a range of from 2.5 to 12.5 emu/g. The carrier, the coating, and the platinum-containing anticancer drug may be at least 85 wt. % of total composition weight.

Inventive compositions may be configured to release at least 80 wt. % of the platinum-containing anticancer drug within 5 days under physiological conditions.

Aspects of the invention provide methods for killing a cancer cell which may comprise contacting any permutation of the composition described herein with the cancer cell.

Aspects of the invention provide methods for making any permutation of the inventive composition described herein, which methods may comprise contacting the carrier, in calcined form, with the platinum-containing anticancer drug prior to applying the coating.

Aspects of the invention provide methods for making any permutation of the inventive composition described herein, which methods may comprise contacting the carrier with chitosan under acidic conditions so as to form the coating, to obtain a coated carrier; and contacting the coated carrier with the platinum-containing anticancer drug, so as to load the platinum-containing anticancer drug into and/or onto the composition.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
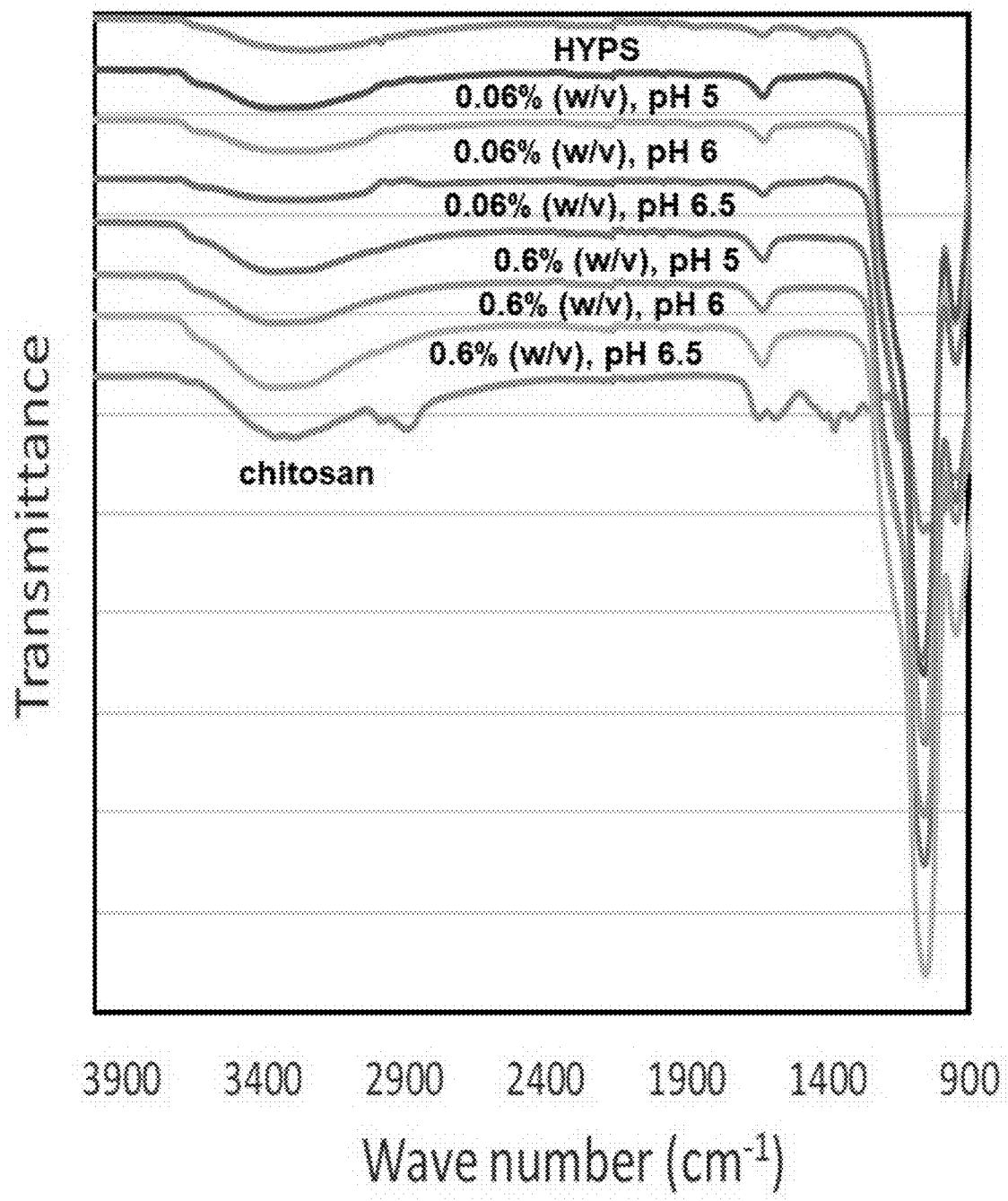
FIG. 1 shows Fourier transform-infrared (FT-IR) spectra of chitosan, hybrid plasma sprayed (HYPS) silica nanoparticles, and various chitosan coated silica nanoparticles within the scope of the invention.

Aspects of the invention provide compositions comprising: a spherical HYPS silica; a metal ferrite of a theoretical formula $MFe_2O_4$, on an outer surface of the silica, M being Ni, Cu, Co, and/or Mn, and M being present in 15 to 45 wt. %, based on total metal ferrite weight, the silica and the metal ferrite forming at least 75, 80, 85, 90, 92.5, 95, 97.5, 98, 99, 99.1, 99.5, or 99.9 wt. % of a carrier, based on total carrier weight; a coating comprising at least 75, 80, 85, 90, 92.5, 95, 97.5, 98, 99, 99.1, 99.5, or 99.9 wt. %, based on total coating weight, of chitosan, the coating contacting the carrier on an inner surface and exposed to the outside environment (e.g., air, fluid carrier, body fluid in vivo) on an outer surface; and a platinum-containing anticancer drug, disposed within and/or on the carrier and/or the coating. The composition may comprise 1, 2, 3, 4, or more types of metal ferrites, or mixed metal ferrites, i.e., 2, 3, 4, or more different doping metals in the ferrite. The metal(s) may be present in the metal ferrite in, e.g., at least 15, 17.5, 20, 22.5, 25, 27.5, 30, 32.5, or 35 wt. % and/or up to 45, 42.5, 40, 37.5, 35, 32.5, 30, 27.5, or 25 wt. %, based on the total metal ferrite weight.

The metal ferrite may have a formula closely corresponding to $MFe_2O_4$, i.e., varying in the atoms of M by up to 20, 15, 10, 7.5, 5, 4, 3, 2.5, 2, 1.5, 1, or 0.5 atom. %, or the metal ferrite may have exactly such a formula, e.g., with one atom of a single metal M per two atoms of Fe and four atoms of oxygen. In the case of plural M atoms, the stoichiometric sum of such M atoms may also be 1±0.2, 0.15, 0.125, 0.1, 0.075, 0.05, 0.04, 0.03, 0.025, 0.02, 0.015, 0.01, or 0.005, in the theoretical formula $MFe_2O_4$.

The metal ferrite will generally be attached onto the surface, or even partially embedded into the surface of the silica carrier. That is, the metal ferrite will generally be a distinct and recognizable morphological feature of the carrier from the silica, although the two (or more) carrier components may be integrally associated, e.g., with no intervening layers or coatings. The silica in the carrier may have an average sphericity of, e.g., at least 0.9, 0.91, 0.915, 0.92, 0.925, 0.93, 0.933, 0.935, 0.94, 0.945, 0.95, 0.955, 0.96, 0.965, 0.96, 0.967, 0.97, 0.975, 0.98, 0.985, 0.9875, 0.99, 0.9925, 0.995, 0.9975, or 0.998. The silica and the metal ferrite generally make out the core of the nanocomposite particles, which are directly coated by the coating, while the coating generally forms the outermost layer—i.e., typically without intervening layers and/or coatings in inventive composite materials.

Inventive materials are generally a composite of the several components in a nanoparticulate form having an irregular granular shape, appearing somewhat like chipped granite with rounded features and jagged features, as well as steps and/or shoulders. The average longest dimension of the nanoparticles may be, for example, at least 1, 2, 2.5, 3, 4, 5, 7.5, or 10 μm and/or up to 40, 35, 30, 25, 20, 15, 12.5, or 10 μm. The average shortest dimension of the nanoparticles may be, for example, at least 0.1, 0.25, 0.5, 0.7, 1, 2, 2.5, 3, 4, or 5 μm and/or up to 15, 12.5, 10, 7.5, 6, 5, 4, 3, 2, or 1 μm.

The composition may be in particle form, having an irregular and/or spheroid morphology. That is, the morphology of the composition is generally not elongated, e.g., on average having no dimension more than 5, 4, 3, 2.5, or 2-fold that of another. The morphology of the composition may also be irregular or amorphous particles, e.g., which are not regular prismic, star-shaped, needle-shaped, or otherwise crystals, and also not flocculent.

The M may preferably comprise Cu for some applications. The M may comprise at least 50, 60, 70, 75, 80, 85, 90, 91, 92, 92.5, 93, 94, 95, 96, 97, 97.5, 98, 99, 99.1, 99.5, or 99.9 wt. %, relative to all non-ferrous metals in the metal-ferrite, of Cu. The M may comprise any combination of Cu, Mn, Ni, and Mo, e.g., Cu with Ni, Cu with Mn, Cu with Mo, Mn with Ni, Mn with Mo, Ni with Mo, Cu with Ni and Mn, Cu with Ni and Mo, Mn with Ni and Mo, Cu with Mn, Ni, and Mo, etc.

The platinum-containing anticancer drug may comprise cisplatin, carboplatin (including dicycloplatin), and/or oxaliplatin. The platinum-containing anticancer drug may comprise at least 75, 80, 85, 90, 92.5, 95, 97.5, 98, 99, 99.1, 99.5, or 99.9 wt. % cisplatin, relative to total platinum-containing anticancer drug weight. The platinum-containing anticancer drug may be present, in mmol per gram of the support, in a range of from 0.05 to 0.25, e.g., at least 0.05, 0.075, 0.1, 0.11, 0.12, 0.125, 0.13, 0.14, 0.15, 0.16, 0.17, or 0.175 and/or up to 0.25, 0.225, 0.2, 0.19, 0.18, 0.175, 0.17, 0.16, 0.15, 0.14, 0.13, or 0.125. Combinations and co-therapeutics may be included with the platinum-containing anticancer drugs, e.g., fluorouracil, ifosfamide, etoposide, retinoic acid, $As_2O_3$, pemetrexed, gemcitabine, paclitaxel, docetaxel, cabazitaxel, vinorelbine, cyclophosphamide, cytosine arabinoside, dexamethasone, G207 (second-generation, multi-mutated herpes simplex virus type 1 vector), Anti-4-1BB, a calcium channel blocker, nifedipine, epirubicin, methotrexate, dactinomycin, bleomycin, hydroxyurea, irinotecan, cytoxan, 2',5'-oligoadenylate, mitomycin, vincristine, 1,2-[bis(1,2-benzisoselenazolone-3(2H)-ketone)] ethane, interferon α-2b, S-1, bevacizumab, coxsackievirus A11, folinic acid, thymoquinone, 5'-deoxy-5-fluorouridine, fluoropyrimidine, trastuzumab, thymidylate synthase inhibitor, epidermal growth factor-receptor antagonist, microtubule interactive agent, etc., or combinations of two or more of any of these. The auxiliary therapeutics may be incorporated (adsorbed) into the nanocomposite, e.g., in and/or on the coating and/or the carrier, or may be administered externally to the coating and/or as a separate agent. For example, the nanocomposite may be encapsulated into another vehicle along with further therapeutics.

The silica may have an average diameter of from 50 to 100 nm, e.g., at least 50, 55, 60, 65, 67.5, 70, 72.5, 75, 77.5, 80, 82.5, or 85 nm and/or up to 100, 95, 90, 87.5, 85, 82.5, 80, 77.5, 75, 72.5, 70, 67.5, or 65 nm, and/or a distribution of the silica may preferably be monomodal, though bimodal, trimodal, or further multi-modal distributions may be useful in certain applications.

The metal ferrite may have an average particle size in a range of from 4 to 15 nm, e.g., at least 4, 4.5, 5, 5.5, 6, 6.25, 6.5, 6.75, 7, 7.25, 7.5, 7.75, 8, 8.25, 8.5, 8.75, 9, 9.5, 10 nm and/or up to 15, 14, 13.5, 13, 12.5, 12, 11.5, 11, 10.75, 10.5, 10.25, 10, 9.75, 9.5, 9.25, 9, 8.75, 8.5, 8.25, 8, 7.75, 7.5, or 7 nm. The metal ferrite may be present in the carrier, relative to the total carrier weight, in a weight percentage of from 15 to 40 wt. %, e.g., at least 15, 17.5, 20, 22.5, 25, 27.5, 30, 32.5, or 35 wt. % and/or up to 40, 37.5, 35, 32.5, 30, 27.5, 25, 22.5, or 20 wt. %.

The chitosan in the coating may have a Mw in a range of from 30 to 250 kDa, e.g, at least 35, 40, 45, 50, 55, 60 65, 70, 75, 80, 85, 90, 95, 100, 125, or 150 kDa and/or up to 250, 225, 200, 190, 180, 175, 170, 165, 160, 155, 150, 145, 140, 135, 130, or 125 kDa. The degree of acetylation of the chitosan may be, e.g., at least 5, 6, 7, 8, 9, 10, 12.5, or 15% and/or up to 50, 45, 40, 35, 32.5, 30, 27.5, 25, 22.5, 20, 19, 18, 17.5, 17, 16, 15, 14, 13, 12.5, 12, 11, or 10%, whereby degrees of acetylation beyond 20% may be from reacetylated forms of chitosan/chitin, which retain sufficient solubility to be coated onto the carrier. The chitosan may be dissolved in organic solvents, such as DMSO, DMF, (glacial) acetic acid, or the like, if not by dilute aqueous acetic acid. The coating may constitute no more than 20, 19, 18, 17.5, 17, 16, 15, 14, 13, 12, 11, 10, 7.5, or 5 wt. % of total composition weight, though some embodiments may call for more than 25, 30, 35, 40, 45, 50 wt. % coating, particularly chitosan-comprising coating. At least 25, 30, 35, 40, 45, 50, 60, 70, 75, 80, 85, 90, 91, 92, 92.5, 93, 94, 95, 96, 97, 97.5, 98, 99, 99.1, 99.5, or 99.9 wt. % of the platinum-containing anticancer drug may be present in the coating.

The carrier may comprise at least 95, 95.5, 96, 96.5, 97, 97.5, 98, 98.5, 98.75, 99, 99.25, 99.5, 99.75, 99.9, 99.99 wt. % or more of the metal ferrite and the silica, based on the total carrier weight, and/or the carrier may have a pore volume in a range of from 0.15 to 0.25 cm³/g. The carrier may have a saturation magnetization in a range of from 2.5 to 12.5 emu/g, e.g., at least 2.5, 3, 3.5, 3.75, 4, 4.25, 4.5, 4.75, 5, 5.25, 5.5, 5.75, or 6 emu/g and/or up to 12.5, 12, 11.5, 11, 10.5, 10, 9.75, 9.5, 9.25, 9, 8.75, 8.5, 8.25, 8, 7.75, 7.5, 7.25, 7, 6.75, 6.5, 6.25, 6, 5.75, 5.5, 5.25, or 5 emu/g. The carrier, the coating, and the platinum-containing anticancer drug may be at least 85, 90, 91, 92, 92.5, 93, 94, 95, 96, 97, 97.5, 98, 99, 99.1, 99.5, or 99.9 wt. % of total composition weight. That is, the composition need not comprise substantially further components other than inevitable contaminants.

Inventive compositions may be configured to release at least 80, 82.5, 85, 87.5, 90, 92.5, or 95 wt. % of the platinum-containing anticancer drug within 5 days under physiological conditions, and/or at pH 5, 5.5, 6, 6.5, or 7 and at least 17.5, 20, 22.5, 25, 27.5, or 30 to 45, 42.5, 40, 37.5, 35, 32.5, 30, 27.5, 25° C.

Aspects of the invention provide methods for killing a cancer cell which may comprise contacting any permutation of the composition described herein with the cancer cell. The cancer cell may be a sarcoma, carcinoma, e.g., small cell lung cancer, squamous cell carcinoma of the head and neck and ovarian cancer, lymphoma, bladder cancer, colorectal cancer, cervical cancer, lung cancer, brain cancer, neuroblastoma, and/or germ cell tumor. The cancer treated may be a testicular cancer.

Aspects of the invention provide methods for making any permutation of the inventive composition described herein, which methods may comprise contacting the carrier, in calcined form, with the platinum-containing anticancer drug prior to applying the coating.

Aspects of the invention provide active ingredients suitable to reduce the viability of cancer cells may be determined by contacting the composition with the cancer cell(s) and then performing cell viability assays. Methods of such assays include, but are not limited to, ATP test, Calcein AM assay, clonogenic assay, ethidium homodimer assay, Evans blue assay, fluorescein diacetate hydrolysis/Propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, and TUNEL assay. The cancer cell may be derived from human cancer cell lines, including, but not limited to, colon cancer cell lines, e.g., HCT15, MDST8, GP5d, HCT116, DLD1, HT29, SW620, SW403 and T84, liver cancer cell lines, e.g. HepG2, PLC/PRF/5, THLE-3, C3A, SNU-182, SNU-398, SNU-387, SNU-423, SNU-475, SNU-449, and Hep 3B2.1-7, lung cancer cell lines, e.g., A549, SHP-77, COR-L23/R, and NCI-H69/LX20, breast cancer cell lines, e.g., MDA-MB-231, MCF7, T47D, and VP303, cervical cancer cell Lines, e.g., HeLa DH, HtTA-1, HR5, and C-4I, ovarian cancer cell lines, e.g., A2780, A2780cis, OV7, and PEO23, and skin cancer cell lines, e.g., C32TG, A375, and MCC26. The cancer cell may be collected from a human patient at risk of or suspected of having, diagnosed with, or being monitored for recurrence of at least one type of cancer, such as testicular, cervical, colon, liver, and/or lung cancer. Cisplatin-resistant cancer cells may be treated or tested, and these cells may be generated by culturing cancer cells with low doses of cisplatin in order to build their resistance to cisplatin while maintaining cell viability. Examples of cisplatin-resistant cancer cells may include, A549 cisplatin-resistant lung cancer cells, MCF-7 cisplatin-resistant breast cancer cells, A2780cis cisplatin-resistant ovarian cancer cells, and SGC7901cis cisplatin-resistant gastrointestinal cancer cells.

A cytotoxic amount may be administered, i.e., a concentration of the active ingredient that reduces the viability of the cancer cells by at least 5, 10, 15, 20, 30, 40, 50, 60, 70, 80, or 90%, relative to cancer cells not treated with the active ingredient. The reduction in viability may occur within 10, 7, 5, 3, or 2 days after the active ingredient is contacted with the cancer cell(s). The cytotoxic amount may be the $IC_{50}$ which is a concentration of the active ingredient which causes the death of 50% of cancer cells in about 24 hours (1 day). For a dosage in 1 mg/L concentration (in sterile saline or other physiologically tolerable/IV solution), the cisplatin injection may be administered at 20 mg/m$^2$ (e.g., ±0.1, 0.25, 0.5, 0.75, 1, 1.5, 2, 2.5, 3, 3.5, 4, 4.5, or 5 mg/m$^2$) intravenously daily for 4, 5, 6, or 7 days per cycle, for testicular cancer, e.g., at least 75, 77.5, 80, 82.5, 85, 87.5, or 90 mg/m$^2$ and/or up to 100, 95, 92.5, 90, 87.5, 85, 82.5, or 80 mg/m$^2$ intravenously per cycle once every 3 to 4 weeks for ovarian cancer, e.g., at least 50, 52.5, 55, 57.5, 60, 62.5, or 65 mg/m$^2$ and/or up to 70, 67.5, 65, 62.5, 60, 57.5, or 55 mg/m$^2$ intravenously per cycle once every 3 to 4 weeks for bladder cancer, etc. Typical dosages of cisplatin or other platinum-comprising anticancer drugs may be, e.g., 0.75, 1, 1.25, 1.5, 1.75, 2, 2.25, or 2.5 mg/kg and/or up to 5, 4.5, 4, 3.75, 3.5, 3.25, 3, 2.75, 2.5, 2.25, 2, 1.75, or 1.5 mg/kg In addition to the platinum-comprising anticancer drug, inventive compositions may include a second active ingredient, such as a chemotherapeutic agent or an anticancer agent, e.g., for the treatment or prevention of neoplasm, tumor, cancer cell division, growth, proliferation, and/or metastasis in a subject (e.g., human, canine, bovine, murine, swine, etc.). The treatment/contacting may involve the induction of death or apoptosis of tumor and/or cancer cells, and/or any other forms of proliferative disorder.

The second anticancer agent may be a mitotic inhibitor, alkylating agent, antimetabolite, cell cycle inhibitor, enzyme, topoisomerase inhibitor, biological response modifier, antiangiogenic (e.g., MMP-2, MMP-9, COX-2 inhibitor), anti-androgen, platinum coordination complex (cisplatin, oxaliplatin, carboplatin), substituted urea (e.g., hydroxyurea), methylhydrazine derivative, adrenocortical suppressant (e.g., mitotane, aminoglutethimide, etc.), hormone, and/or hormone antagonist (e.g., adrenocorticosteriod such as prednisone, progestin such as hydroxyprogesterone caproate, estrogen such as diethylstilbestrol, antiestrogen such as tamoxifen, androgen such as testosterone propionate, and aromatase inhibitor such as anastrozole, and exemestane), or any therapeutic described herein. Exemplary anticancer agents may include alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; anti-microtubule agents including etoposide, vinblastine, vincristine, teniposide, docetaxel, paclitaxel, vinorelbine, vindesine; cytotoxic antibiotics including daunorubicin, doxorubicin, idarubicin, mitomycin, actinomycin, epirubicin; topoisomerase inhibitors including irinotecan, mitoxantrone, topotecan, and mixtures of two or more of any of these.

Aspects of the invention provide methods for making any permutation of the inventive composition described herein, which methods may comprise contacting the carrier with chitosan under acidic conditions so as to form the coating, to obtain a coated carrier; and contacting the coated carrier with the platinum-containing anticancer drug, so as to load the platinum-containing anticancer drug into and/or onto the composition.

Relevant pharmaceutical agents may include, for example, alkylating agents, thiotepa, cyclophosphamide, semustine, chlormethine HCl, busulfan, chlorambucil, formylmerphalan, carmustine, altretamine, lomustine, D and/or L-phenylalanine mustard, Nitrocaphane, ifosfamide, mitobronitol; antimetabolite, cytarabine, fluorouracil, methotrexate, hydroxycarbamide, tegafur, meisoindigotin, mercaptopurine, actinomycin D, mitomycin, doxorubicin HCl, bleomycin, A5 HCl, epirubicin HCl, pirarubicin HCl, daunorubicin HCl, plant natural resistance umbellifera, homoharringtonine vincristine sulfate, hydroxycamptothecin, etoposide, vindesine sulfate, vinblastine sulfate, vinorelbine bitartrate, paclitaxel, docetaxel, vinblastine, vinorelbine, zedoary turmeric, ginseng polysaccharide, colchicine, 9-amino camptothecin alkali, 7-ethylcamptothecin, elemene, aminoglutethimide, tamoxifen, flutamide, gonadorelin, leuprorelin acetate, lelozol, carboplatin, procarbazine HCl, amsacrine, dacarbazine citrate, asparaginase, cisplatin, mitoxantrone HCl, and/or oxaliplatin. Inventive materials may contain, e.g., at least 0.00001, 0.0001, 0.001, 0.01, 0.1, 0.5, 1, 1.5, 2, 2.5, 3, 4, 5, 7.5, 10, 12.5, 15, 20, or 25 wt. % and/or up to 50, 45, 40, 35, 30, 25, 22.5, 20, 17.5, 15, 12.5, 10, 9, 8, 7, 6, 5, 4, 3, 2, 1, 0.5, 0.1, 0.01, 0.001, 0.0001, or 0.00001 wt. % (potentially even excluding any of these), relative to total nanocomposite weight, thereof, individually or in combination.

Inventive materials may exclude one or more genetic materials and/or biologics, e.g., DNA, RNA, miRNA, dsRNA, shRNA, plasmids, proteins (e.g., albumin, collagen, etc.), biotin, dyes, and quantum dots, or may comprise no more than 15, 10, 7.5, 5, 4, 3, 2.5, 2, 1, 0.5, 0.1, 0.01, 0.001, 0.0001, or 0.00001 wt. %, relative to the total organic pharmaceutical weight, of such genetic materials and/or biologics, individually or in combination.

Inventive materials may exclude one or more of, or contain no more than 5, 4, 3, 2.5, 2, 1, 0.5, 0.1, 0.01, 0.001, 0.0001, or 0.00001 wt. %, relative to total pharmaceutically active material weight, of abatacept, abciximab, abobotulinum toxin A, acridine, adalimumab, adalimumab-atto, ado-trastuzumab emtansine, aflibercept, agalsidase beta, alarin, albiglutide, aldesleukin, alefacept, alemtuzumab, alglucosidase alfa, alirocumab, alteplase, amifostine, aminoglutethimide, anakinra, asfotase alfa, asparaginase, asparaginase Erwinia chrysanthemi, atezolizumab, basiliximab, becaplermin, belatacept, belimumab, bevacizumab, bezlotoxumab, blinatumomab, brentuximab vedotin, canakinumab, capromab pendetide, cathflo activase, certolizumab pegol, cetuximab, collagenase, collagenase clostridium histolyticum, daclizumab, daclizumab, daratumumab, darbepoetin alfa, dasatinib, denileukin diftitox, denosumab, dinutuximab, dornase alfa, dulaglutide, ecallantide, eculizumab, elosulfase alfa, elotuzumab, epoetin alfa, erythropoietin, etanercept, etanercept-szzs, evolocumab, filgrastim, filgrastim-sndz, follitropin alpha, galsulfase, glucarpidase, golimumab, golimumab injection, ibritumomab tiuxetan, idarucizumab, idursulfase, incobotulinum toxin A, infliximab, infliximab-dyyb, interferon alfa-2b, interferon alfa-n3, interferon beta-1a, interferon beta-1b, interferon gamma-1b, ipilimumab, ixekizumab, laronidase, mepolizumab, methoxy polyethylene glycol-epoetin beta, metreleptin, natalizumab, necitumumab, nilotinib, nivolumab, obiltoxaximab, obinutuzumab, ocriplasmin, ofatumumab, olaratumab, omalizumab, onabotulinum toxin A, oprelvekin, palifermin, palivizumab, panitumumab, parathyroid hormone, pegaspargase, pegfilgrastim, peginterferon alfa-2a, peginterferon alfa-2b, peginterferon beta-1a, pegloticase, pembrolizumab, pertuzumab, ramucirumab, ranibizumab, rasburicase, raxibacumab, reslizumab, reteplase, rilonacept, rimabotulinum toxin B, rituximab, romiplostim, sargramostim, sebelipase alfa, secukinumab, siltuximab, sorafenib, tbo-filgrastim, tenecteplase, tocilizumab, trastuzumab, ustekinumab, vedolizumab, and/or ziv-aflibercept.

Inventive nanocomposites may exclude precious metals, such as Au, Ag, and/or Pd, or metals such as Ca, Co, Ni, Zn, Mn, Ti, Zr, W, Mo, Ru, Rh, Ir, Os, Re, and/or Sn or contain only inevitable traces thereof, or may contain no more than 5, 4, 3, 2.5, 2, 1, 0.5, 0.1, 0.01, 0.001, 0.0001, or 0.00001 wt. %, relative to total metal weight in the nanocomposite (or of the total nanocomposite weight), of such metals, individually or in combination.

Inventive materials generally do not produce heat when subjected to a magnetic field, and/or may increase the local temperature by no more than 0.1, 0.25, 0.33, 0.5, 0.67, 0.75, 1, 1.25, 1.5, 1.75, 2, 2.5, or 3° C.

Inventive materials may have coatings substantially comprising chitosan, e.g., at least 50, 60, 70, 75, 80, 85, 90, or 95 wt. % of the total coating weight, or may exclude or comprise no more than 5, 4, 3, 2.5, 2, 1, 0.5, 0.33, 0.1, 0.05, 0.01, 0.001, 0.0001, or 0.00001 wt. %, relative to total coating weight, of polymers of lactic and/or glycolic acid.

Beyond the ferrite and silica, inventive carriers may exclude further carriers, such as $TiO_2$, $ZrO_2$, ITO, $SnO_2$, and/or $InO_2$, or may comprise no more than 15, 10, 7.5, 5, 4, 3, 2, 1, 0.5, 0.1, 0.01, 0.001, 0.0001, or 0.00001 wt. %, relative to the total carrier weight, of such carriers, individually or in combination.

Aspects of the invention include different chitosan loadings, e.g., at least 0.05, 0.06, 0.07, 0.08, 0.09, 0.1, 0.11, 0.125, 0.15, 0.175, 0.2, 0.225, 0.25, 0.275, 0.3, 0.325, 0.35, 0.375, 0.4% (w/v) and/or up to 0.75, 0.7, 0.675, 0.65, 0.625, 0.6, 0.575, 0.55, 0.525, 0.5, 0.475, 0.45, 0.425, 0.4, 0.375, 0.35, 0.325, 0.3% (w/v) at different pH including, e.g., 4, 4.5, 5, 5.25, 5.33, 5.5, 5.67, 5.75, 6, 6.25, 6.33, 6.5, 6.76, 6.75, and/or 7, or any range using such endpoints, to coat nanoscale (HYPS) hydrophilic spherical silica particles. Aspects of the invention provide, e.g., at least 15, 17.5, 20, 22.5, 25, 27.5, or 30 wt. % and/or up to 45, 42.5, 40, 37.5, 35, 32.5, 30, 27.5, or 25 wt. %, spinel ferrites, such as $NiFe_2O_4$, $CuFe_2O_4$, $CoFe_2O_4$, and $MnFe_2O_4$, impregnated over HYPS (e.g., 30 wt. % metal-ferrite in the silica) and then treated or loaded with chitosan, e.g., at 0.6% (w/v) and/or at pH 6. Aspects of the invention comprise modifying and/or controlling the release of pharmaceutical, such as cisplatin, via the composition of the nanoformulations, and/or modifying the cytotoxicity against cancer tissue, e.g., the MCF-7 cell line. Aspects of the invention provide differentiated Pt complex cumulative release depending on the spinel ferrite and chitosan fabrication route, improving the pH-based drug release, improving the temperature-based drug release, and/or allowing diagnosis-based treatment such as hyperthermia.

Aspects of the invention control the cytotoxic efficiency of nanoparticles on cancerous tissue, such as the human embryonic kidney cells (HEK293) and breast cancer cell line (MCF7). For example, while $CuFe_2O_4$/HYPS is not cytotoxic, cisplatin and its loaded derivatives, such as Groups D and E described below, exhibit reduced cell viability when administered with $CuFe_2O_4$/HYPS. Modified cisplatin forms, such as those containing groups B, D, and E described below, can show a dose dependent response for both cell lines. HEK293 may be less sensitive to cisplatin containing certain groups, e.g., B, D, and E, than MCF7. Cell viability of MCF7 at the lowest tested concentration of cisplatin, i.e., group B was 58.17%, for loaded-cisplatin, i.e., group D was 63.36%, and for $CuFe_2O_4$-HYPS with chitosan and cisplatin, i.e., group E was 70.73%. Cell viability of HEK293 was 73.47% for B, 80.24% for D, and 95.07% for E.

Aspects of the invention provide chitosan wrapped or coated cisplatin loaded $CuFe_2O_4$-HYPS nanoparticles, as a drug delivery system, particularly to target cancerous cells with at least the efficiency of pure cisplatin. The EC50 value of group C, discussed below, shows that wrapping or coating a cisplatin on 30 wt. % $CuFe_2O_4$ on HYPS composite with chitosan followed by pH adjustment (Group C) showed no significant effect on cell viability compared with Group D and E, discussed below. The concentration of cisplatin per gram of $CuFe_2O_4$-HYPS nanosupport may be, e.g., at least 0.01, 0.025, 0.05, 0.075, 0.1, 0.11, 0.12, 0.125, 0.13, 0.14, 0.15, 0.175, 0.2, 0.225, 0.25, or 0.3 mmol and/or up to 0.5, 0.45, 0.4, 0.35, 0.3, 0.25, 0.225, 0.2, 0.175, or 0.15 mmol.

Aspects of the invention provide chitosan wrapping or coating processes in which the initial acidic pH of the chitosan solution may be increased to 6.5 by dropwise addition of 1 M NaOH solution. After pH adjustment, cisplatin loaded $CuFe_2O_4$/HYPS may be added and then the pH may be increased to 7. The mixture may be kept under stirring for another 24 hours, then separated off, e.g., centrifuged, washed, and dried under vacuum, e.g., for 48 hours at 37° C. For example, a filtered solution of a 0.15 mmol cisplatin sample may show a decrease in the mmol cisplatin/gram of $CuFe_2O_4$-HYPS from 0.15 to 0.03. Aspects of the invention may thus comprise controlled and/or directed cisplatin release into solution via chitosan pH adjustment, e.g., as Group C may show a less inhibitory effect compared to Group D and Group E (wrapping or coating with chitosan before cisplatin loading, which may be the best nanoformulation).

Figure 10:
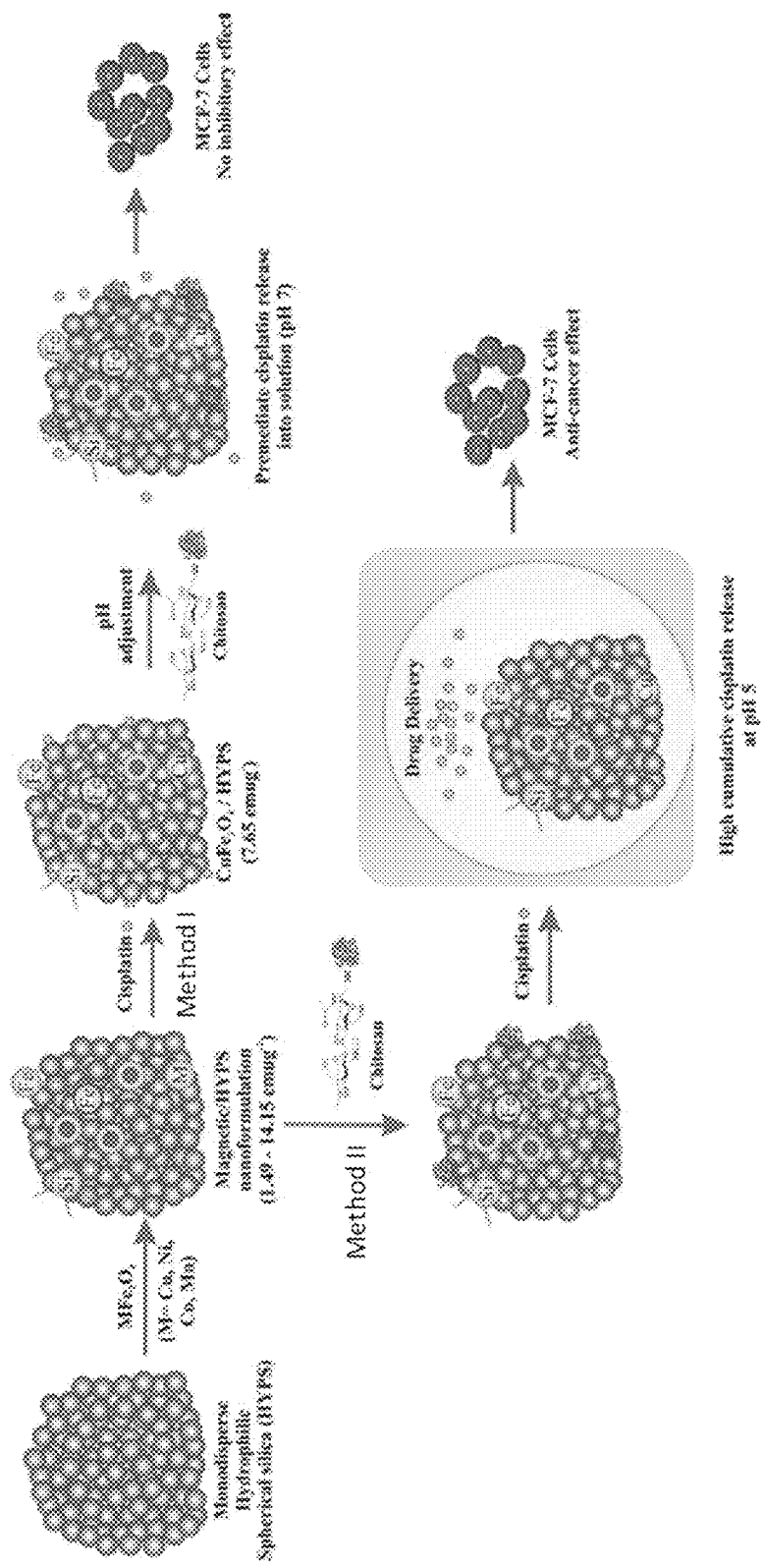
FIG. 10 shows a schematic representation of the exemplary nanoformulations using cisplatin on the $MFe_2O_4$ on HYPS silica carriers described herein.

Aspects of the invention allow cisplatin release during chitosan pH adjustment to be avoided, while increasing the biocompatible of the nanocomposite as shown in FIG. 10. Aspects of the invention provide cisplatin-loaded $CuFe_2O_4$-coated silica nanoparticles suitable to target cancerous cells, and/or $CuFe_2O_4$-HYPS silica nanoparticles as a drug delivery system.

A cisplatin-doped, spinel ferrite/structured silica-based magnetic tumor imaging diagnostic tool for targeted cancer therapy, can often be too toxic, particularly at higher concentration levels The invention nanocomposites can have improved biocompatibility with chitosan coatings, attenuated toxicity, improved endocytosis efficiency, improved bioavailability, and/or improved anticancer activity.

EXAMPLES

Material and Methods: Hybrid plasma sprayed silica (HYPS) was purchased from Superior Silica, USA. Chitosan of molecular weight 50 to 190 kDa ($M_w$) was purchased from Sigma Aldrich. The chemicals used for the preparation of various spinel ferrites, $Ni(NO_3)_2 \cdot 6H_2O$, $Cu(NO_3)_2 \cdot 3H_2O$, $Mn(NO_3)_2 \cdot 4H_2O$, $Co(NO_3)_2 \cdot 6H_2O$, $Fe(NO_3)_3 \cdot 9H_2O$, and cisplatin were obtained from Sigma Aldrich. All chemicals were used as-such without any further modification or purifications.

Fabrication of chitosan on hybrid plasma sprayed silica (HYPS): 0.06 and 0.6% (w/v) chitosan were dissolved in acetic acid solutions 2% (v/v) in water. The pH of the aqueous chitosan-acetic acid solution was increased to 5, 6, and 6.5 using a 1M NaOH solution dropwise and left under stirring for 48 hours. HYPS silica (1 g) was then added to the solution to obtain a mixture, and the mixture was stirred overnight and separated off using centrifugation at 4000 rpm for 10 min. Then the material was repeatedly washed, then dried in desiccator under vacuum for 48 hours at 37° C.

Preparation of 30 wt. % $MFe_2O_4$ (total spinel ferrite loading) on HYPS (M=Ni, Cu, Co and Mn): The hybrid plasma sprayed silica (HYPS) support was pre-dried at 120° C. for 24 hours. For $NiFe_2O_4$ on HYPS, 0.74 g (2.54 mmol) of $Ni(NO_3)_2 \cdot 6H_2O$ and 1.03 g (2.55 mmol) of $Fe(NO_3)_3 \cdot 9H_2O$ were mixed with 1.4 g of HYPS using mortar pestle, then the ground mixture was calcined at 850° C. for 6 hours. The same synthetic procedure was used for the synthesis of $CuFe_2O_4$-HYPS, $CoFe_2O_4$-HYPS, and $MnFe_2O_4$-HYPS, i.e., using equimolar amounts of HYPS and $Cu(NO_3)_2 \cdot 2.5H_2O$ (MW: 232.59 g/mol), $Co(NO_3)_2 \cdot 6H_2O$ (MW: 291.03 g/mol), and $Mn(NO_3)_2 \cdot xH_2O$ (MW: 178.95 g/mol, anhydrous basis). An appropriate amount (30 mg, 0.1 mmol) of cisplatin, $Pt(NH_3)_2Cl_2$, was dissolved in normal saline solution (NSS) and loaded following the procedure described in *Appl. Nanosci.* 2018, 8, 1205-1220, which is incorporated by reference herein in its entirety.

Fabrication of chitosan coating over cisplatin-doped 30 wt. % $MFe_2O_4$ on HYPS (M=Ni, Cu, Co and Mn)

Method I: Firstly, 30 mg (0.1 mmol) of cisplatin was loaded onto a $CuFe_2O_4$-HYPS support by dissolving in the amount of cisplating in normal saline solution (NSS). Secondly, chitosan was dissolved using 2% (v/v) aq. acetic acid solution, to give a 0.6% (wt/v) of acidified aqueous chitosan. Thirdly, 1 g (3.33 mmol) of cisplatin-loaded $CuFe_2O_4$-HYPS was added to the acidified aqueous chitosan solution, and the pH of the chitosan solution was increased to 6.0 using 1M NaOH (aq) solution, added dropwise, and the resulting pH 6 mixture was left stirring for 48 hours under ambient conditions. Fourthly, the pH 6 chitosan-cisplatin-metal-ferrite mixture was stirred for 48 hours, and the solid was separated off by centrifugation at 4000 rpm for 10 minutes, repeatedly washed, then the solid was dried in a desiccator using vacuum for 48 hours at 37° C.

Method (II): Firstly, a 0.6% (wt/v) solution of chitosan was prepared by dissolving chitosan in a 2% (v/v) aq. acetic acid solution. Secondly, 1 g (3.33 mmol) of $CuFe_2O_4$-HYPS was added to the a acidified aqueous chitosan solution and the pH was increased to 6.0 by adding 1M NaOH (aq) solution dropwise, and the resulting pH 6 mixture was left stirring for 48 hours under ambient conditions Thirdly, the solution mixture was mixed and stirred for 48 hours, and the solid was separated off by centrifugation at 4000 rpm for 10 minutes, repeatedly washed, then the solid was dried in a desiccator using vacuum for 48 hours at 37° C. Fourthly, an appropriate amount (30 mg, 0.1 mmol) of cisplatin and chitosan-coated 30 wt. % $CuFe_2O_4$ on HYPS were placed in a normal saline solution (NSS) and loaded to yield a cis-platin doped, chitosan-coated, 30 wt. % $CuFe_2O_4$ on HYPS nanocomposite.

CHARACTERIZATION: Powder x-ray diffraction pattern (PXRD) analysis for chitosan-treated HYPS and $MFe_2O_4$ on HYPS was conducted using a Rigaku MiniFlex 600 instrument (Japan). Surface textures of nanocomposites were analyzed using a Micromeritics ASAP-2020 plus instrument (USA). Chitosan functional groups on HYPS were analyzed by FT-IR using attenuated total reflection (ATR) technology with a PERKIN ELMER instrument (USA). The magnetization of $MFe_2O_4$-HYPS nanoformulations was analyzed using a LDJ Electronics Inc. Model 9600 vibrating-sample magnetometer (VSM) instrument. Scanning electron microscopy (SEM) was performed using a JEOL JSM-6610LV instrument, whereby the prepared powder was dispersed onto doubled-sided tape holder and examined at 20 kV. Energy dispersive spectroscopy (EDS) spectra were optained using Aztec software from the Oxford Company. The suspensions for transmission electron microscopy (TEM) analysis were prepared from dry samples with ethanol, followed by ultrasonic treatment for 30 minutes. A droplet (5 µL) of dilute suspension was deposited onto a 300-mesh pure carbon grid, and then kept under vacuum for 1 hour for further drying. The grids were examined using a JEOL JEM2100F transmission electron microscope.

DRUG RELEASE STUDY: The percentage cumulative cisplatin release was studied using a series of $MFe_2O_4$ on HYPS and chitosan-coated $MFe_2O_4$ on HYPS formulations. Cellulose membrane dialysis tubing was activated, and drug delivery was performed by immersing a bag containing 30 mg of drug formulations in 50 mL of phosphate buffered saline (PBS) at pH 5.6. The release was performed under constant temperature at 37° C. At regular time intervals, specific volumes (10 mL) of solution were removed and analyzed using UV-visible spectroscopy.

In-Vitro Study on MCF-7 & HEK293 Cells

To test the cytotoxic efficiency of the exemplary nanocomposites, the human embryonic kidney cell line HEK293 and the human mammary adenocarcinoma cell line MCF7 were used. Cells were maintained in Dulbecco's Modified Eagle Medium (DMEM), supplemented with 10% heat inactivated fetal bovine serum (HI-FBS), 1% Penicillin Streptomycin (100×), and 1% Eagle's minimum essential medium non-essential amino acids (MEM NEAA) (100×) all from Gibco Life Technologies. Cell cultures were kept in a humidified incubator at 37° C. with 5% $CO_2$. Cells were plated on a 96-well plate at a density of 20,000 cells per well. Cultured cells were shifted to a starvation medium, i.e., 0.5% HI-FBS containing media, for 24 hours before treatment.

Grouping of In Vitro Study (Cell Line)

Group A: $CuFe_2O_4$ on HYPS

Group B: cisplatin (alone)

Group C: chitosan-coated, cisplatin-doped $CuFe_2O_4$ on HYPS (Method I)

Group D: cisplatin-doped $CuFe_2O_4$ on HYPS

Group E: cisplatin-doped, chitosan-coated $CuFe_2O_4$ on HYPS (Method II)

Cells were treated for 48 hours using the following conditions: Group A ($CuFe_2O_4$ on HYPS), group B (cisplatin), group C (chitosan-coated, cisplatin-doped $CuFe_2O_4$ on HYPS), group D (cisplatin-doped $CuFe_2O_4$ on HYPS) and group E (cisplatin-doped, chitosan-coated $CuFe_2O_4$ on HYPS). The cytotoxic effects of HYPS and the cytotoxic effects of $CuFe_2O_4$ were tested separately on cultured cells and no effect was found. Therefore, $CuFe_2O_4$ on HYPS (Group A) was taken as a control group. Treatment concentrations of 0.025, 0.05, 0.1, and 0.5 mg/mL were used for Groups A, C, D, and E (not Group B). To accurately reflect the concentration of cisplatin, i.e., Group B, as encapsulated within these nanoparticles, drug loading experiments were used. Therefore, group B treatment concentrations were 0.001125, 0.00225, 0.0045, and 0.0225 mg/mL. Both HEK293 and MCF7 cells were cultured and treated simultaneously.

Cell Viability—Mtt Assay

The cytotoxic effect of exemplary drug formulations were tested using the 3-(4,5-dimethylthiazol-2-yl)-2,5-diphenyltetrazolium bromide (MTT) cell viability assay, which is based on the ability of viable cells to reduce MTT to formazan crystals. The assay was performed as described in *J. Immunol. Methods* 1983, 65(1-2), 55-63, which is incorporated by reference herein in its entirety. Briefly, MTT from Sigma-Aldrich was dissolved in phosphate-buffered saline (PBS) at 5 mg/mL. A working solution of MTT was prepared at a final concentration of 0.5 mg/mL. After washing, 100 μL of the MTT working solution were dispensed in all wells and incubated at 37° C. for three hours. An MTT background control was included, in which the MTT working solution was added to empty wells with no cells. Based on the time dependent study, the recommended incubation time was fixed at 48 hours. 0.04N HCl in isopropanol was added to the wells to dissolve the formazan crystals. The change in color intensity was measured at 570 nm (wavelength) using a SYNERGY-neo2 BioTek ELISA reader. Each condition was performed in triplicate. The reading of each triplicate was averaged and subtracted from the averaged MTT background control reading. Each condition was compared to the control wells, i.e., wells with no treatment.

Equation 1, below, was used to calculate the percentage cell viability:

$$\% \text{ Cell Viability} = \frac{\text{averaged sample read}}{\text{averaged control read}} \times 100. \quad \text{Eq. 1}$$

Statistical Analysis

The cell viability assay data represent either five independent experiments or as indicated in figure legends. Statistical analysis was performed using Prism 8 software from GraphPad. Analysis was performed using two-way ANOVA with Dunnett's multiple comparison post hoc test, with  $p<0.01$; * $p<0.001$; **** $p<0.0001$ versus control.

Surface Area

The surface area and pore size distributions of HYPS and $CuFe_2O_4$ on HYPS were analyzed using the Brunauer-Emmett-Teller (BET) nitrogen adsorption technique. HYPS texture exhibited the surface area of 170 $m^2/g$, a pore volume of 0.35 $cm^3/g$, and an average pore size distributions of 8.3 nm. After (ferrite) spinel loading, about a 28% reduction in BET surface area was observed, with a significant decrease in the pore volume, i.e., from 0.35 $cm^3/g$ to 0.18 $cm^3/g$. The trend clearly shows the accumulation of spinel ferrite nanoparticles at, on, and/or in the pores of HYPS. Exemplary ferrite-HYPS may have a BET surface area, e.g., of at least 0.12, 0.13, 0.135, 0.14, 0.145, 0.15, 0.1525, 0.155, 0.1575, 0.16, 0.1625, 0.165, 0.1675, 0.17, 0.1725, 0.175, 0.1775, or 0.18 $cm^3/g$ and/or up to 0.25, 0.24, 0.23, 0.225, 0.22, 0.2175, 0.215, 0.2125, 0.21, 0.2075, 0.205, 0.2025, 0.20, 0.1975, 0.195, 0.1925, 0.19, 0.1875, 0.185, 0.1825, or 0.18 $cm^3/g$.

Referring now to the drawings, wherein like reference numerals designate identical or corresponding parts throughout the several views.

FIG. 1 shows the FT-IR spectra of exemplary chitosan, HYPS, and chitosan-coated HYPS nanoparticles, from either 0.06 or 0.6% (w/v) solutions at three different pH values, i.e., 5, 6, or 6.5. In the spectrum of the exemplary chitosan, the band in the 3300-3600 $cm^{-1}$ region is attributable to OH and NH stretching, the peak at 1644 $cm^{-1}$ is attributable to the stretching frequency of the amide group, the peak at 1584 $cm^{-1}$ is attributable to the bending vibration of the amine group, the peaks at 2974 and 2892 $cm^{-1}$ are attributable to C—H stretching, and the peaks at 1058 and 1032 $cm^{-1}$ are attributable to C—O stretching vibrations. In the FT-IR spectrum of the exemplary HYPS, the peaks at 1053, 790, and 470 $cm^{-1}$, can be attributed to silanol absorption peaks. In the chitosan-coated HYPS samples, in addition to these silanol peaks, a new peak is evident around 1631 $cm^{-1}$ indicating the presence of chitosan. The intensity of the band in the 3300 to 3600 $cm^{-1}$ region are attributable to the stretching of —O—H, —N—H, and inter/intra molecular hydrogen bonding, which may increase for chitosan-coated silica nanoparticles.

The intensity of the peak corresponding to the chitosan amide group was found to increase with increasing chitosan concentration, here, from 0.06 to 0.6 wt. %. This indicates that as the concentration of chitosan solution increased, more chitosan gets deposited on the surface of silica nanoparticles. For the samples using the exemplary 0.6 wt. % chitosan solution, the intensity of the chitosan-based peaks also increased with increased pH of coating solution. Due to the nature of chitosan, which is soluble in acidic pH, as the pH of the solution increases chitosan may start to precipitate and/or coagulate. However, when the chitosan solution of lower concentration, i.e., 0.06 wt. %, was used, the influence of pH was less clear. The sample tested in pH 5 solution showed high intensity.

Figure 2A:
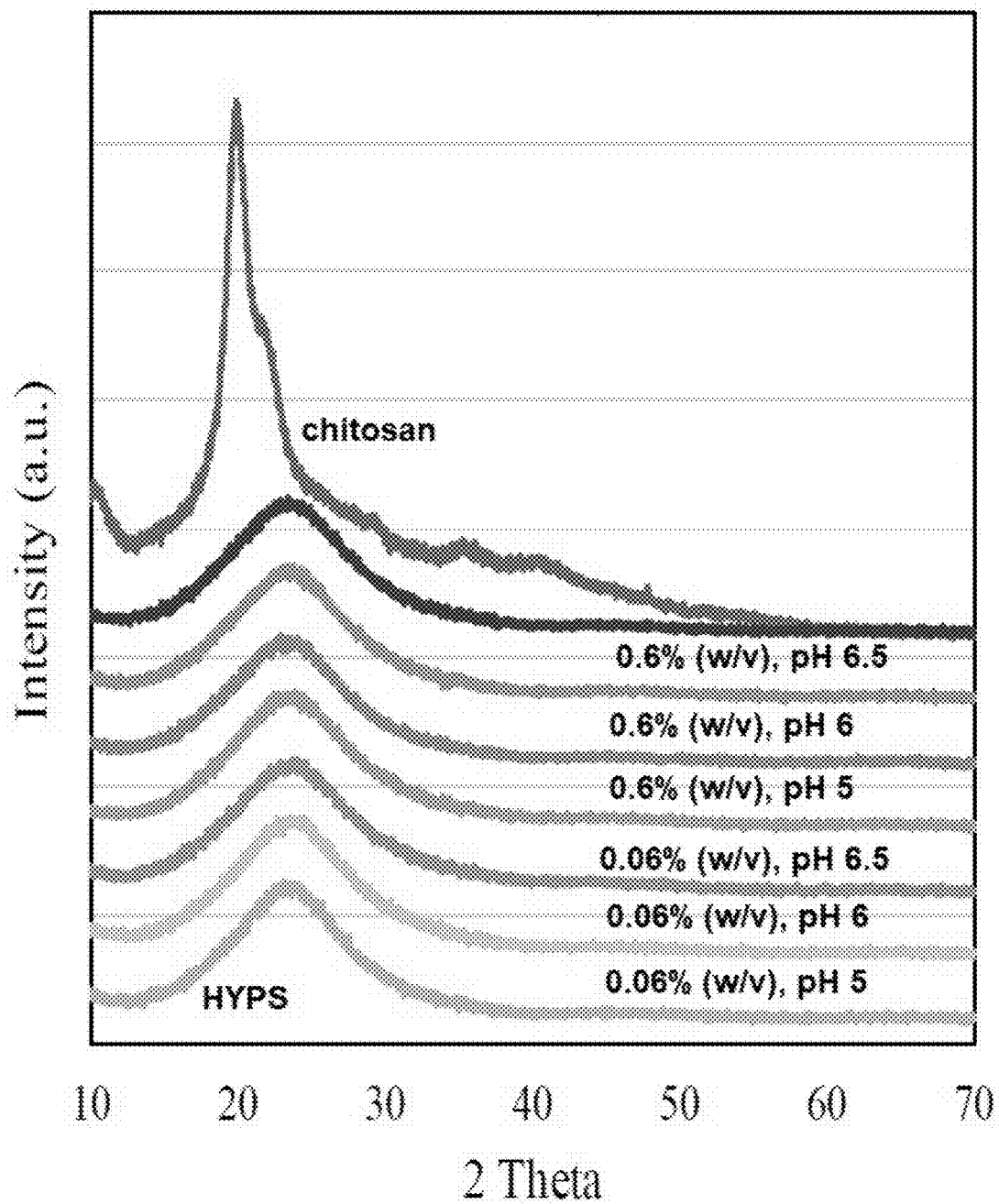
FIG. 2A shows x-ray diffraction (XRD) patterns of chitosan, HYPS silica nanoparticles, and various chitosan coated silica nanoparticles within the scope of the invention.

FIG. 2A shows the x-ray diffraction (XRD) patterns of chitosan, HYPS, and chitosan-coated HYPS silica nanoparticles. The XRD pattern of chitosan showed a crystalline intense peak at 22° and a small peak in the 2θ region of 10°. In the case of HYPS, only a broad band in the range of 23° (2θ) was visible, showing the amorphous nature of silica nanoparticles. The exemplary chitosan-coated HYPS exhibited a similar diffraction pattern to that of silica. The presence of chitosan was not found to alter the amorphous nature of silica. The amorphous structure of silica was retained even after chitosan coating, as seen in the central patterns, indicating that the drug loading efficiency of silica nanoparticles are not affected by chitosan coating. The chitosan coating may enhance the biocompatibility of the drug carrier system while still retaining the drug loading efficiency of silica carrier.

Figure 2B:
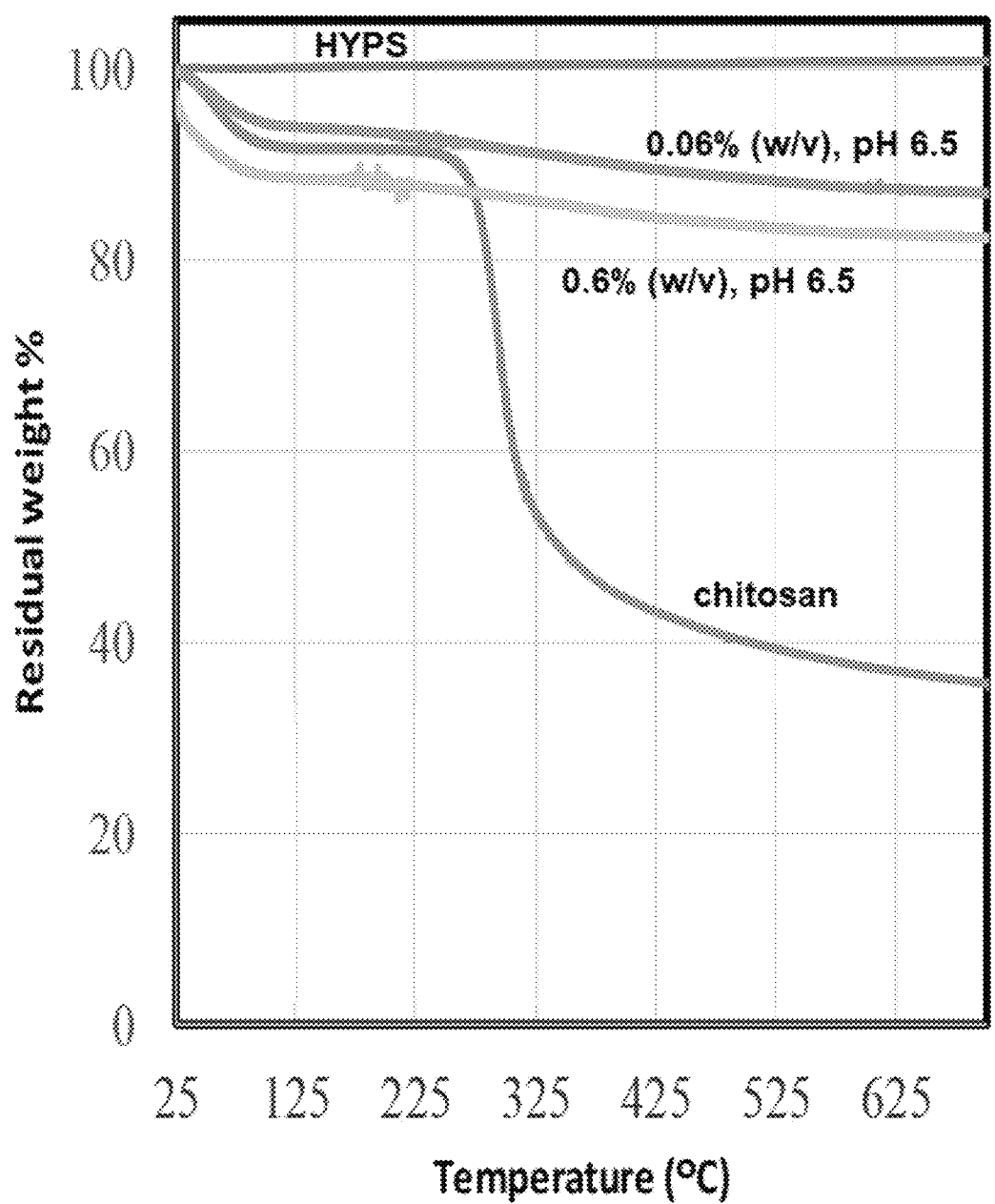
FIG. 2B shows thermogravimetric analysis (TGA) plots of HYPS silica, 0.06 w/v % chitosan loaded HYPS at pH 6.5, 0.6 w/v % chitosan loaded HYPS at pH 6.5, and chitosan.

FIG. 2B shows the thermogravimetric analysis (TGA) thermograms of chitosan, pure silica nanoparticles (HYPS), chitosan coated-silica nanoparticles coated using a 0.06 wt. % chitosan solution, and chitosan coated-silica nanoparticles coated using a 0.6 wt. % chitosan solution. All organic-containing samples showed an initial weight loss during heating to 120° C., due to the loss of bound water. The main degradation of chitosan starts around 280° C., and scission of polymer backbone occurs during heating up to 500° C., producing low molecular weight hydrocarbons and $CO_2$. The residual weight of chitosan at 700° C. was 36%. The thermograms of the exemplary chitosan-coated HYPS silica nanoparticles showed a similar pattern. A slow degradation was observed until 600° C. HYPS. It can be seen that the residual weight of the sample is in proportion to its chitosan content. The sample coated using the lower percentage chitosan solution, i.e., 0.06 wt. % chitosan, showed high residue content of 87.2%, and the sample coated using the higher percentage chitosan solution, i.e., 0.06 wt. % chitosan, showed a lower residual weight content of 82.4%. For the sample coated with high percentage chitosan solution, more chitosan is coated onto the surface of silica nanoparticle. Since, this extra chitosan gets degraded during heating, this sample showed comparatively less residue.

Figure 3A:
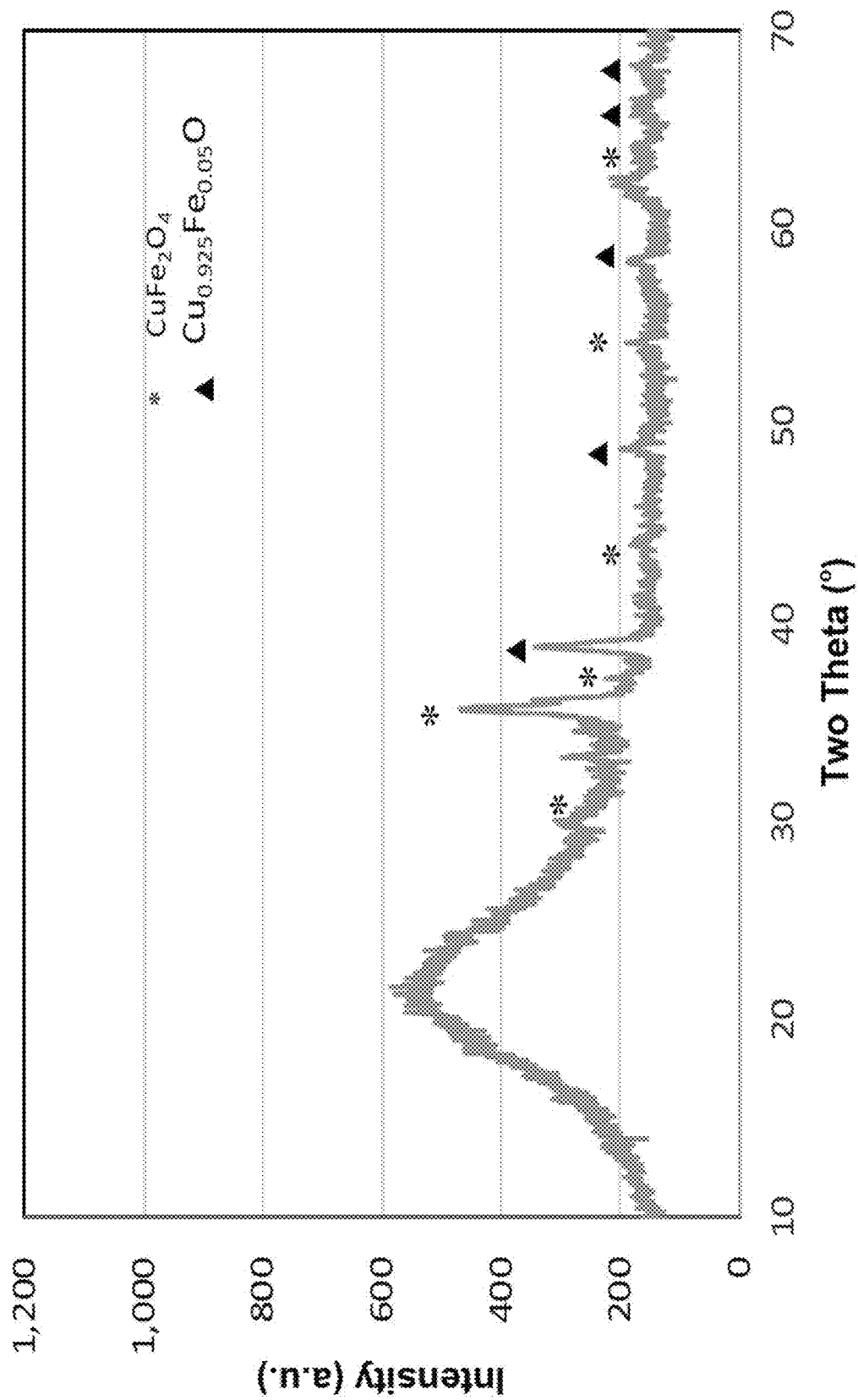
FIG. 3A shows an XRD pattern of an exemplary 30% $CuFe_2O_4$/HYPS specimen.
Figure 3B:
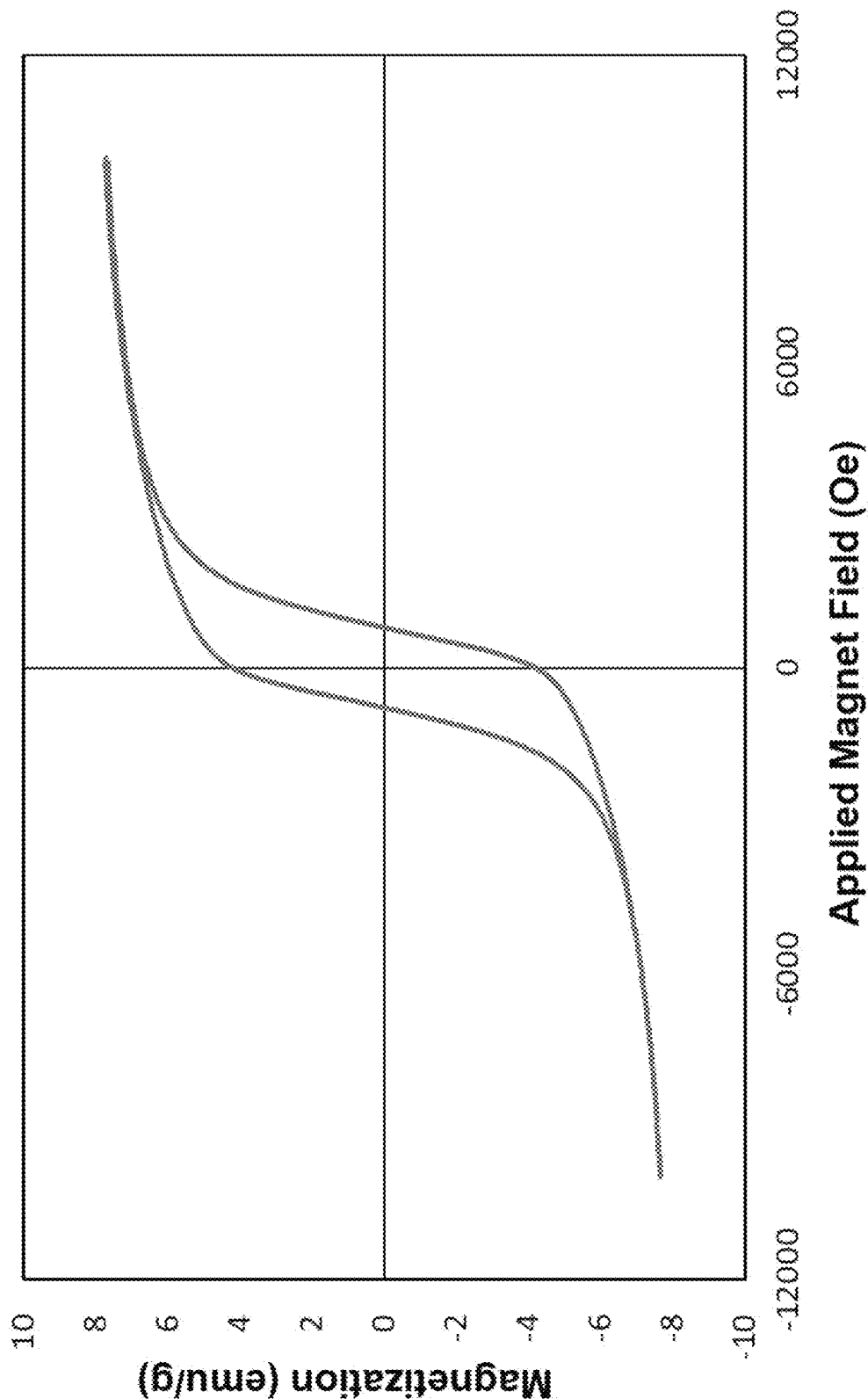
FIG. 3B shows a vibrating sample magnetometer (VSM) spectra of an exemplary 30% $CuFe_2O_4$/HYPS specimen.

FIGS. 3A and 3B shows the XRD diffraction patterns of 30% $CuFe_2O_4$ loaded onto HYPS using the dry impregnation technique described above. The presence of the characteristics broad peak due to amorphous siliceous framework of HYPS was observed between 15 to 30° 2θ. In the case of metal oxides, the diffraction patterns correlate with cubic phase of copper ferrite (JCPDS 77-0010). However, the presence of relatively less crystalline $CuFe_2O_4$ nanoparticles may explain the presence of weak peaks and increased broadness, which usually indicates the presence of small nanoparticles. The broadening trend may indicate a lack of crystallization at spherical nanopores of the HYPS.

FIG. 3B show the saturation magnetization curve for the $CuFe_2O_4$ on HYPS sample, analyzed by vibrating-sample magnetometry (VSM, which is also referred to as Foner magnetometer). The saturation magnetization of $CuFe_2O_4$/HYPS was observed to be 7.65 emu/g. Chitosan-coated magnetic nanoparticle-impregnated HYPS nanoparticles were obtained using method I and II and used as drug carrier for cisplatin.

Figure 4A:
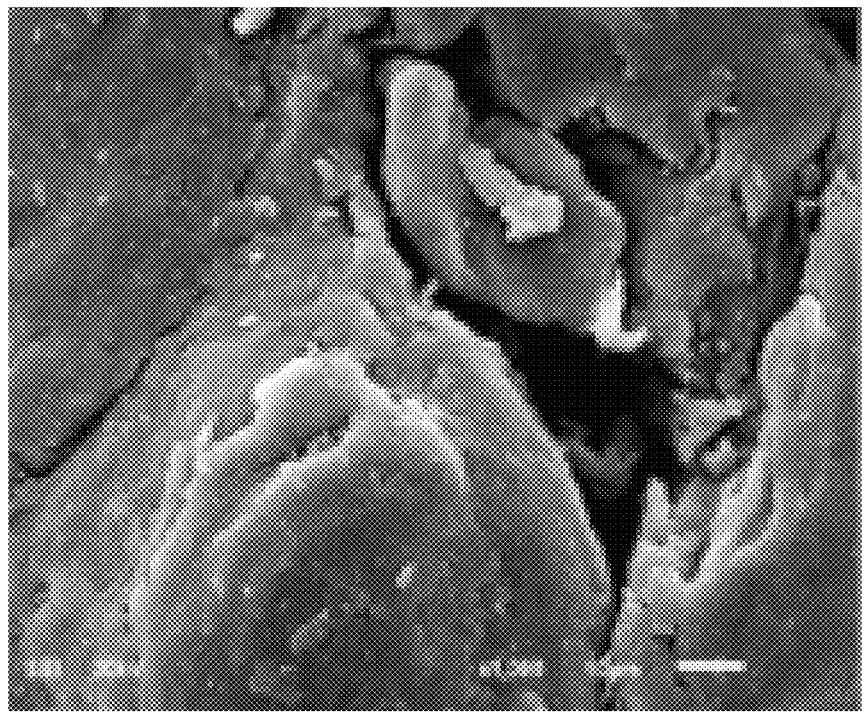
FIG. 4A shows a scanning electron microscopy (SEM) image of an exemplary chitosan-coated 30% $CuFe_2O_4$ on HYPS specimen at 1 μm.
Figure 4B:
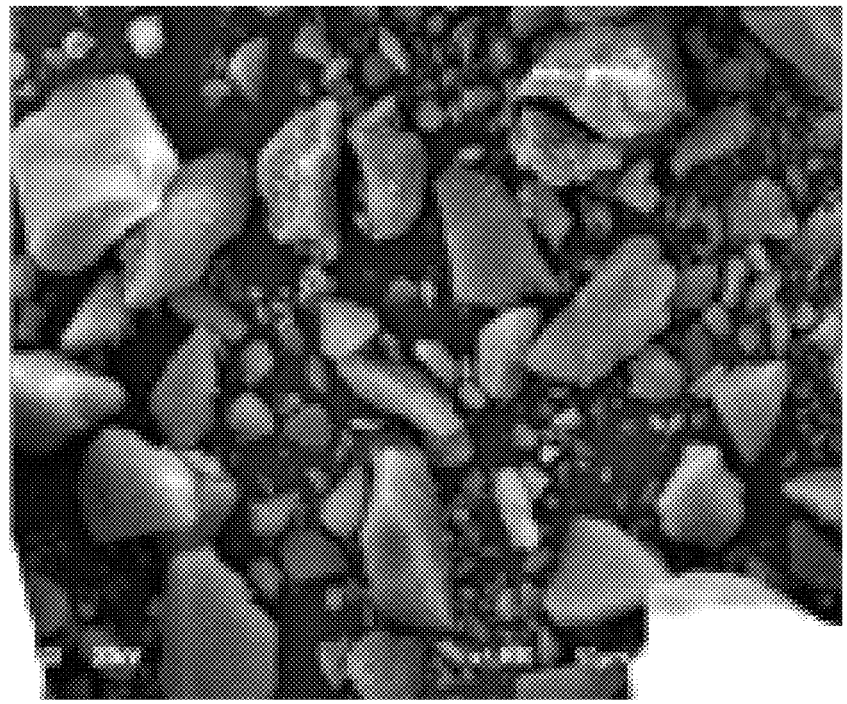
FIG. 4B shows an SEM image of an exemplary chitosan-coated 30% $CuFe_2O_4$ on HYPS specimen at 10 μm.
Figure 4C:
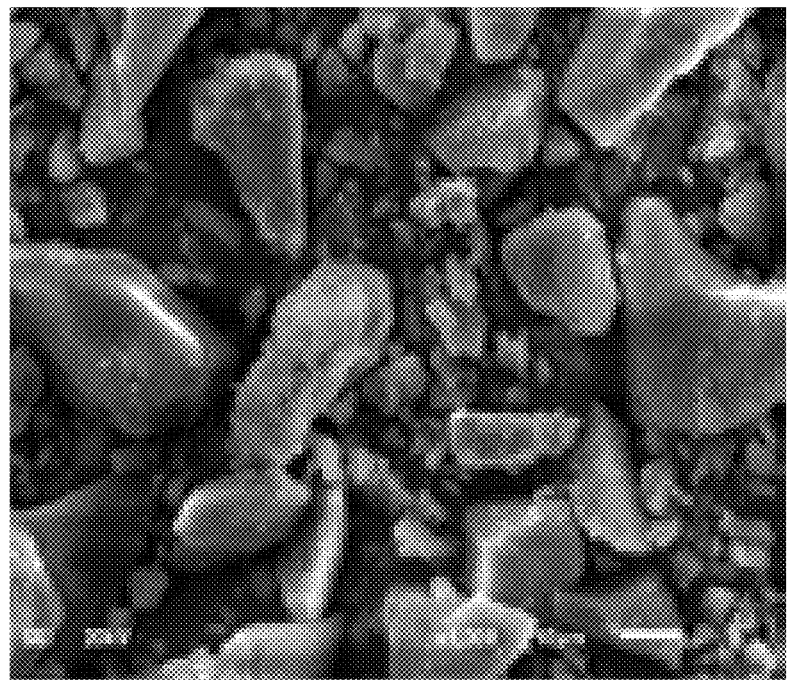
FIG. 4C shows an SEM image of an exemplary uncoated 30% $CuFe_2O_4$ on HYPS specimen at 10 μm.
Figure 4D:
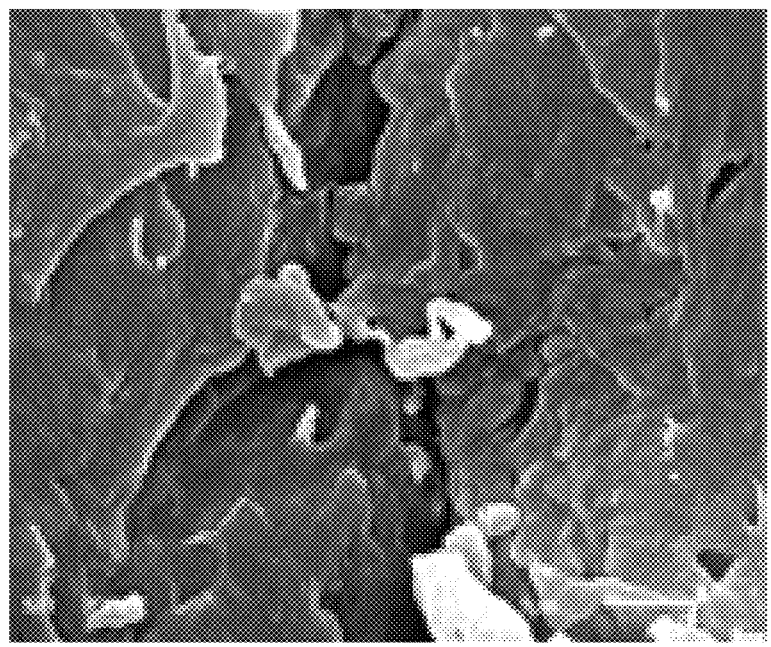
FIG. 4D shows an SEM image of an exemplary uncoated 30% $CuFe_2O_4$ on HYPS specimen at 1 μm.
Figure 4E:
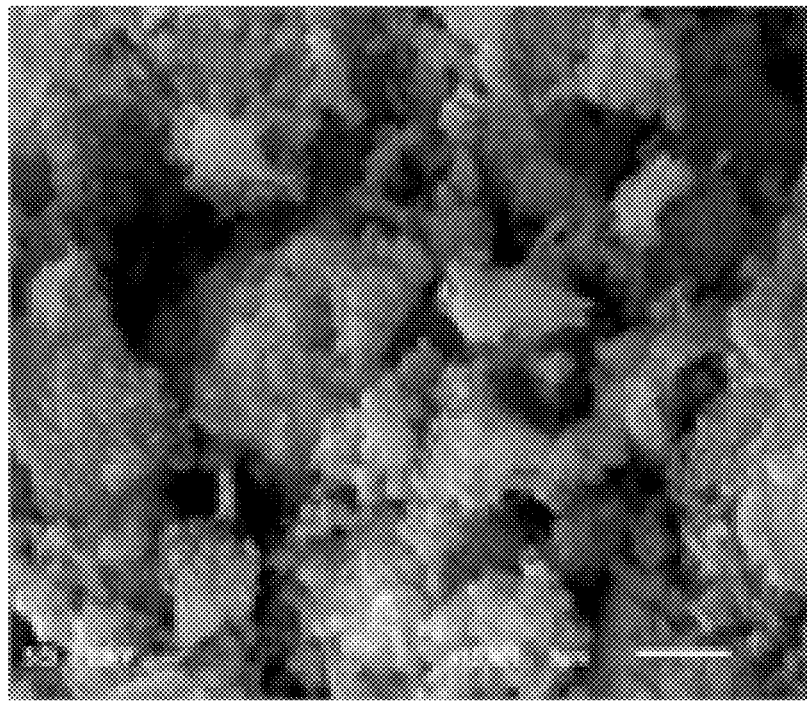
FIG. 4E shows an SEM image of an exemplary chitosan-coated, cisplatin-loaded 30% $CuFe_2O_4$ on HYPS specimen at 10 μm.
Figure 4F:
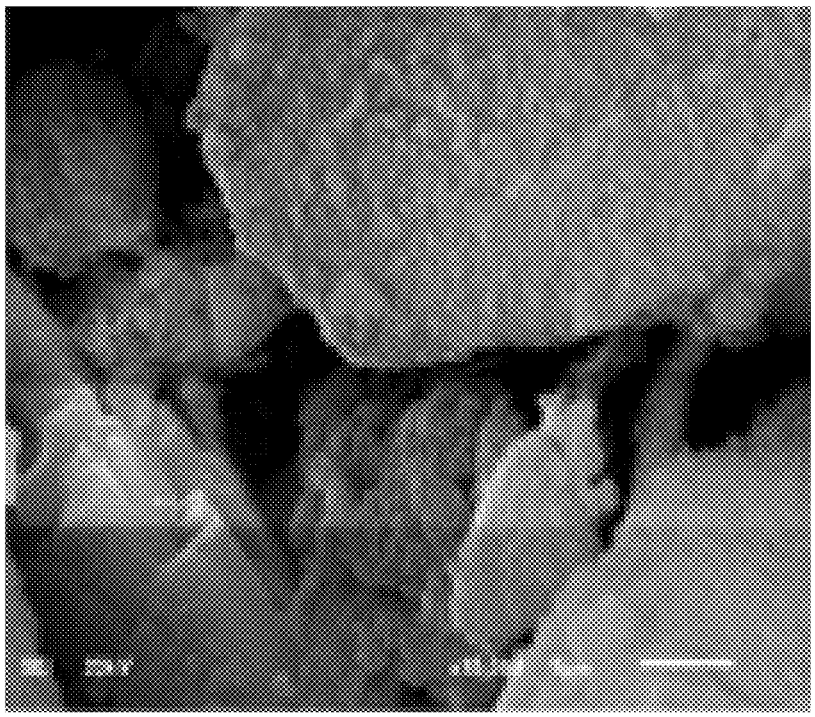
FIG. 4F shows an SEM image of an exemplary chitosan-coated, cisplatin-loaded 30% $CuFe_2O_4$ on HYPS specimen at 1 μm.

The surface morphology of chitosan, 30% $CuFe_2O_4$ on HYPS and cisplatin-doped, chitosan-coated $CuFe_2O_4$ on HYPS were analyzed by SEM-EDS, as shown in FIG. 4A to 4C. Chitosan-coated samples viewed at two different magnifications, 10 μm (FIG. 4B) and 1 μm (FIG. 4A) had a rough surface, with some particles agglomerated and forming irregular shapes. In case of copper-ferrite-loaded HYPS, different shaped chunks of crystals appear, indicating that a mixed metal oxide formation occurs in major proportion, while agglomerated Cu nanoclusters are also detected, as seen in FIGS. 4C and 4D. Chitosan-coated $CuFe_2O_4$ on HYPS shown in FIGS. 4E and 4F indicate an increase in crystal size indicating coating effect, though the sample still exhibited porous structure enabling the encapsulation of the drug in the cavities.

Figure 4G:
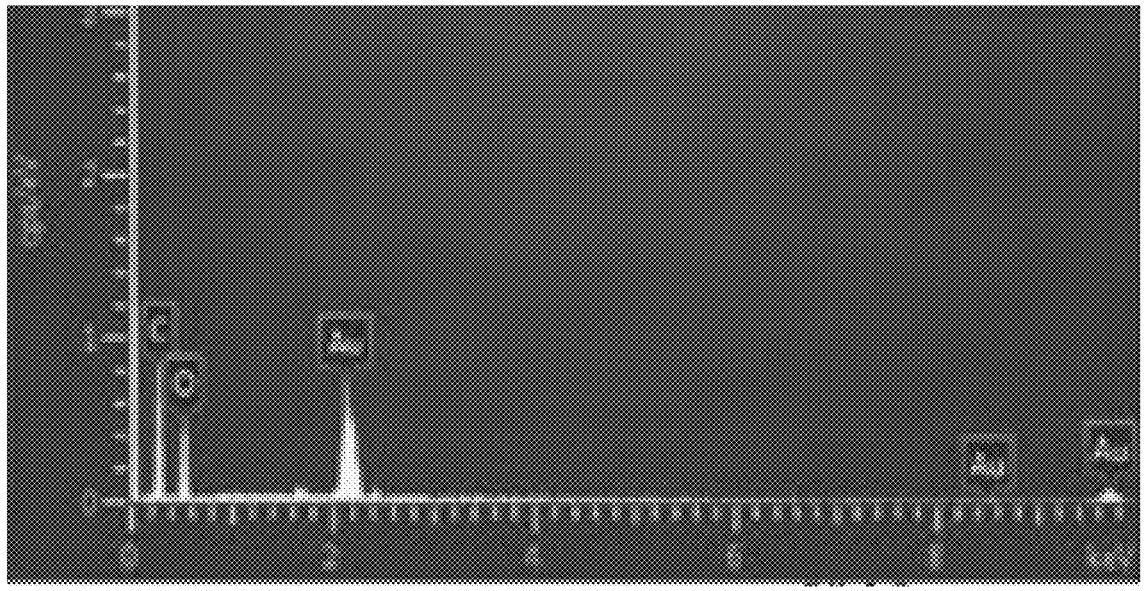
FIG. 4G shows an energy-dispersive x-ray spectroscopy (EDS) an exemplary uncoated 30% $CuFe_2O_4$ on HYPS specimen.
Figure 4H:
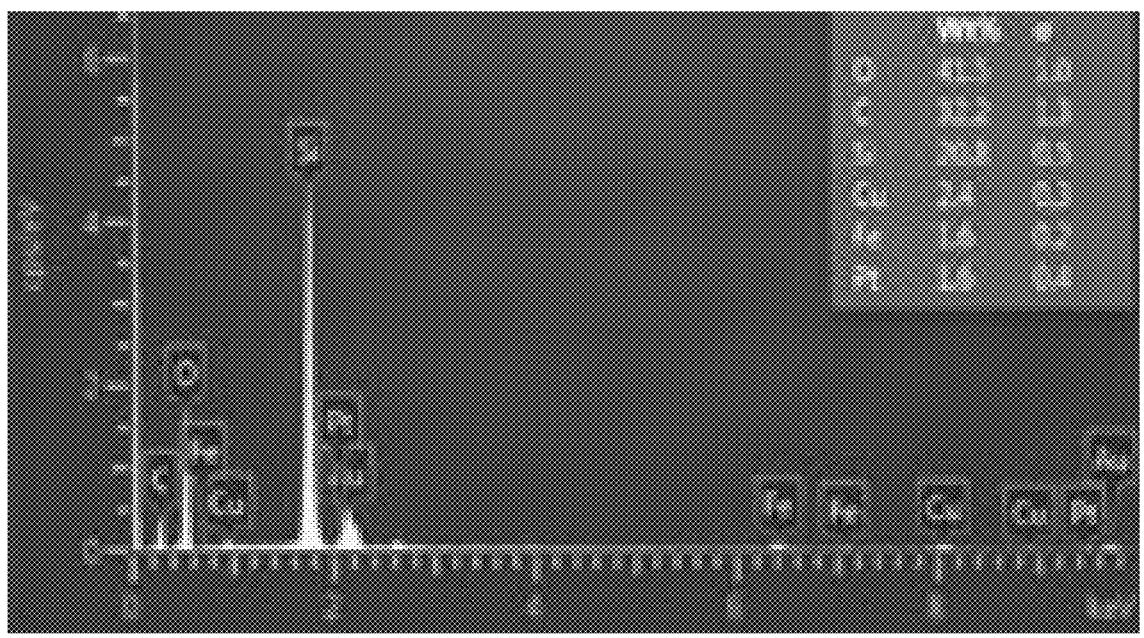
FIG. 4H shows an energy-dispersive x-ray spectroscopy (EDS) an exemplary chitosan-coated, cisplatin-loaded 30% $CuFe_2O_4$ on HYPS specimen.
Figure 4I:
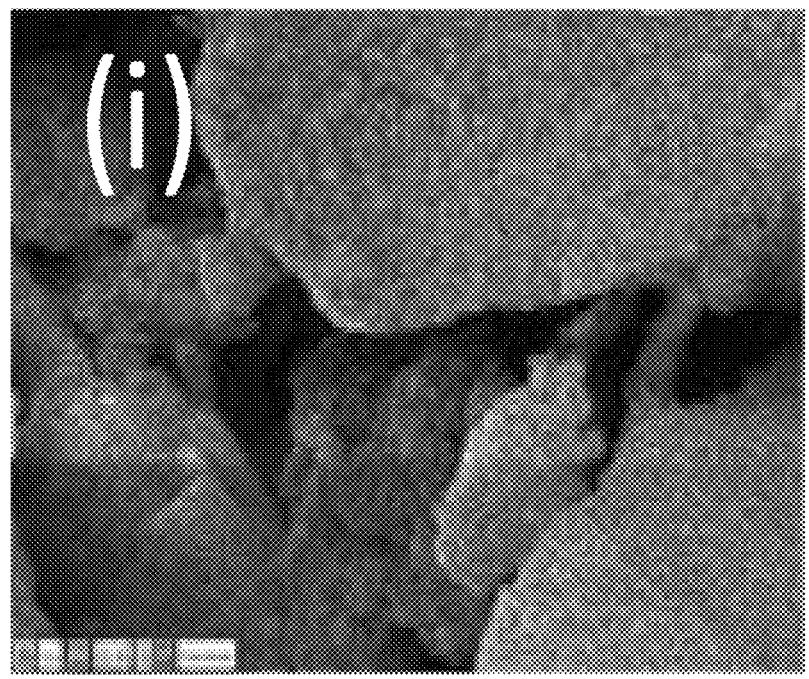
FIG. 4I shows an SEM morphological image of an exemplary chitosan-coated, cisplatin-loaded 30% $CuFe_2O_4$ on HYPS specimen.
Figure 4J:
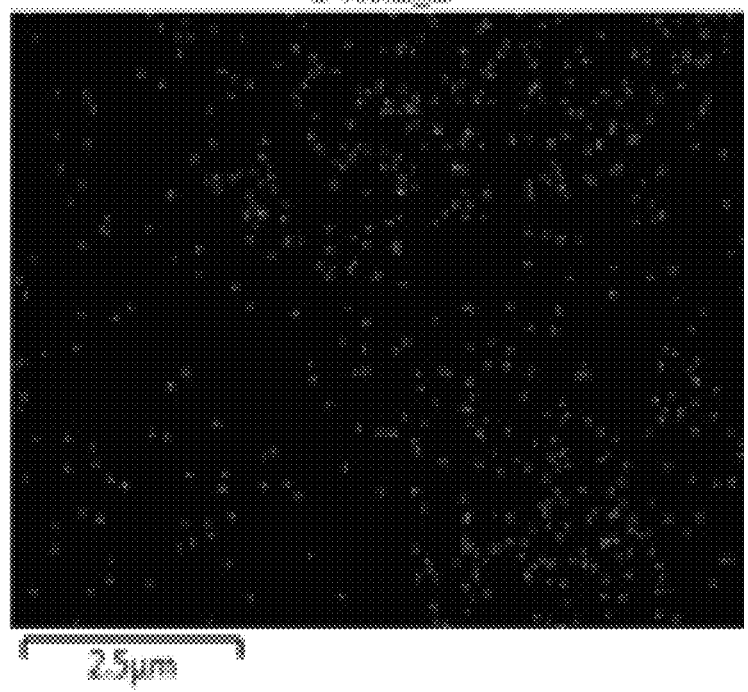
FIG. 4J shows elemental dot mapping analysis of an exemplary chitosan-coated, cisplatin-loaded 30% $CuFe_2O_4$ on HYPS specimen for carbon (C)
Figure 4K:
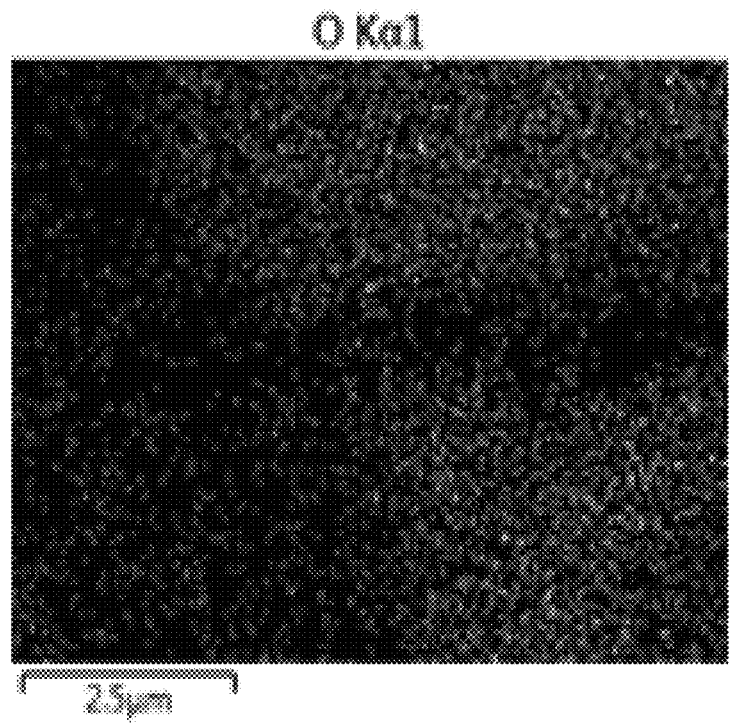
FIG. 4K shows elemental dot mapping analysis of an exemplary chitosan-coated, cisplatin-loaded 30% $CuFe_2O_4$ on HYPS specimen for oxygen (O)
Figure 4L:
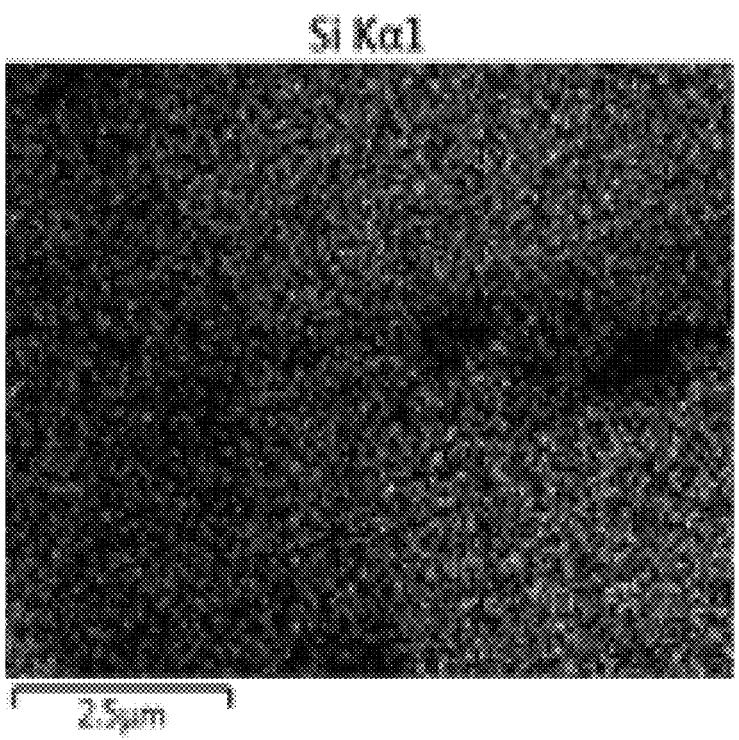
FIG. 4L shows elemental dot mapping analysis of an exemplary chitosan-coated, cisplatin-loaded 30% $CuFe_2O_4$ on HYPS specimen for silicon (Si)
Figure 4M:
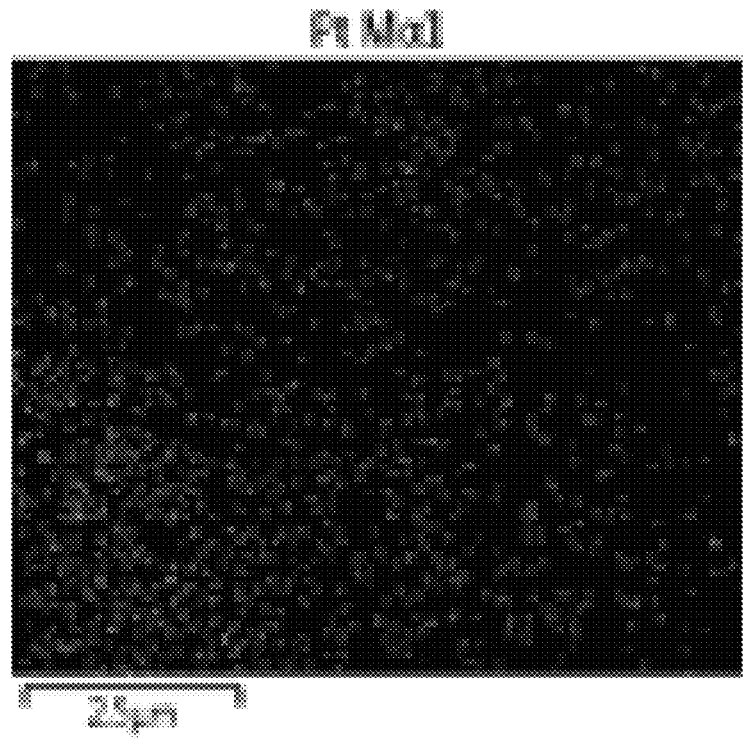
FIG. 4M shows elemental dot mapping analysis of an exemplary chitosan-coated, cisplatin-loaded 30% $CuFe_2O_4$ on HYPS specimen for platinum (Pt)
Figure 4N:
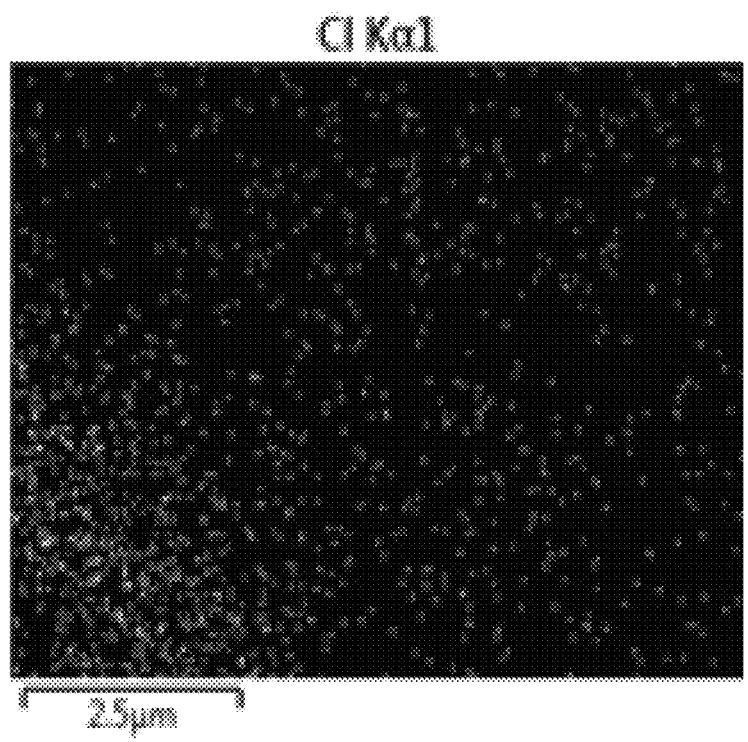
FIG. 4N shows elemental dot mapping analysis of an exemplary chitosan-coated, cisplatin-loaded 30% $CuFe_2O_4$ on HYPS specimen for chlorine (Cl)
Figure 4O:
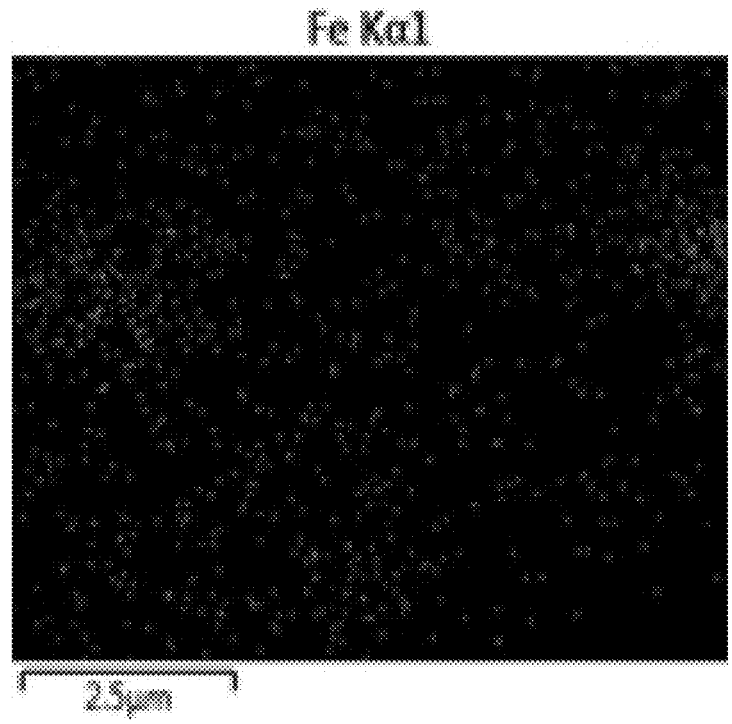
FIG. 4O shows elemental dot mapping analysis of an exemplary chitosan-coated, cisplatin-loaded 30% $CuFe_2O_4$ on HYPS specimen for iron (Fe)
Figure 4P:
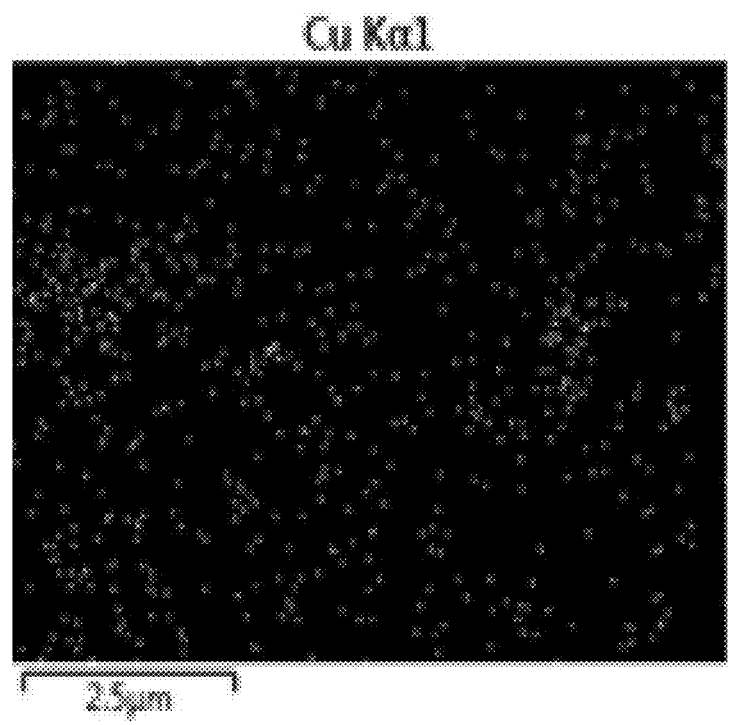
FIG. 4P shows elemental dot mapping analysis of an exemplary chitosan-coated, cisplatin-loaded 30% $CuFe_2O_4$ on HYPS specimen for cupper (Cu)
Figure 5A:
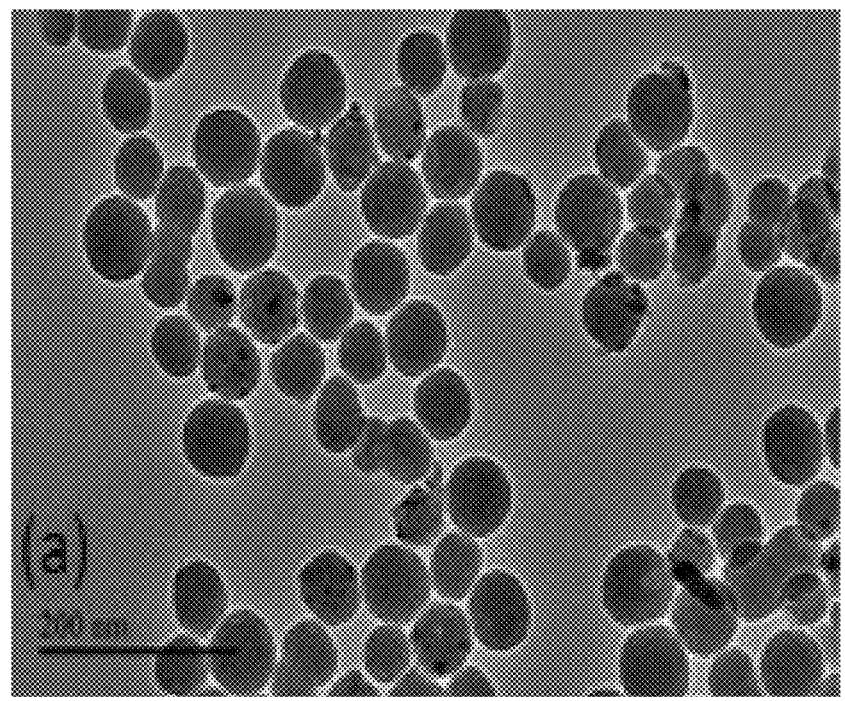
FIG. 5A show a transmission electron microscope (TEM) image of an exemplary 30% $CuFe_2O_4$ on HYPS silica specimen on 200 nm scale.
Figure 5B:
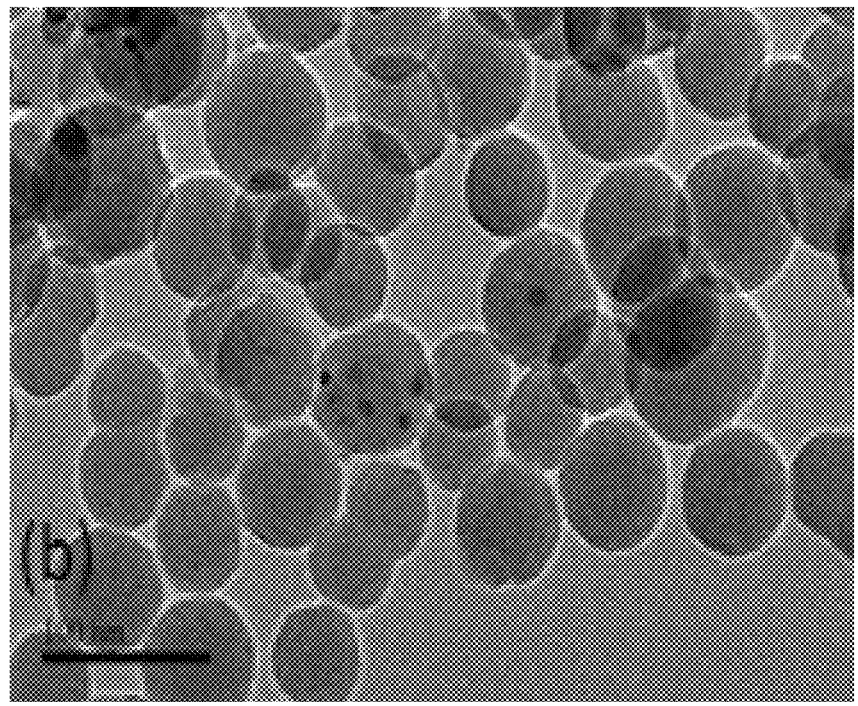
FIG. 5B show a TEM image of an exemplary 30% $CuFe_2O_4$ on HYPS silica specimen on 100 nm scale.
Figure 5C:
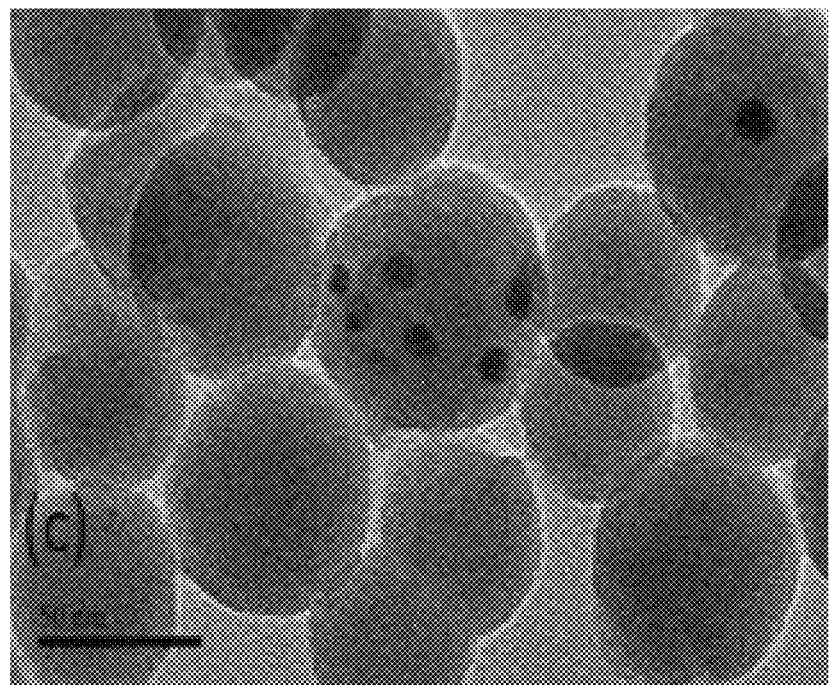
FIG. 5C show a TEM image of an exemplary 30% $CuFe_2O_4$/HYPS specimen on 50 nm scale.
Figure 5D:
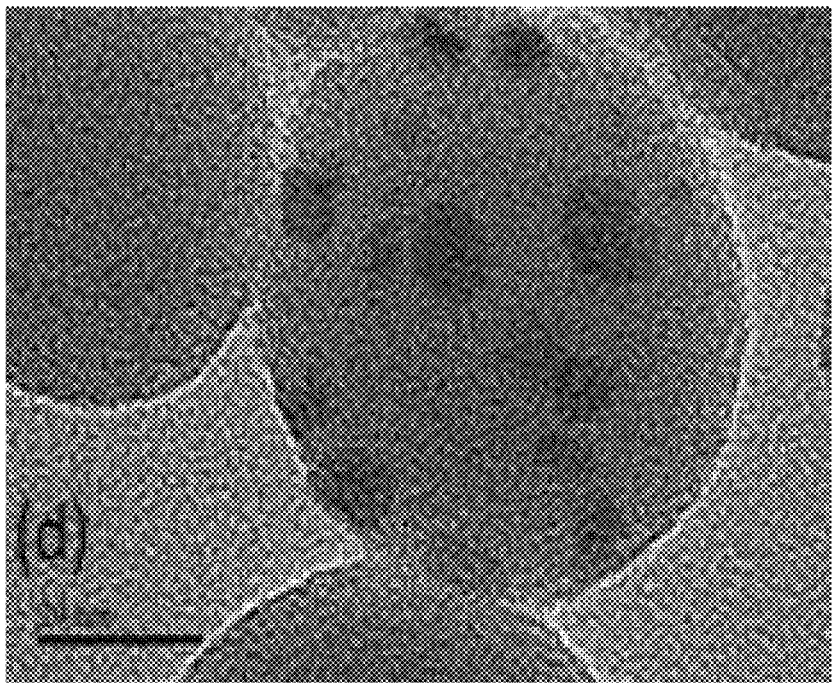
FIG. 5D show a TEM image of an exemplary 30% $CuFe_2O_4$/HYPS specimen on 20 nm scale.
Figure 5E:
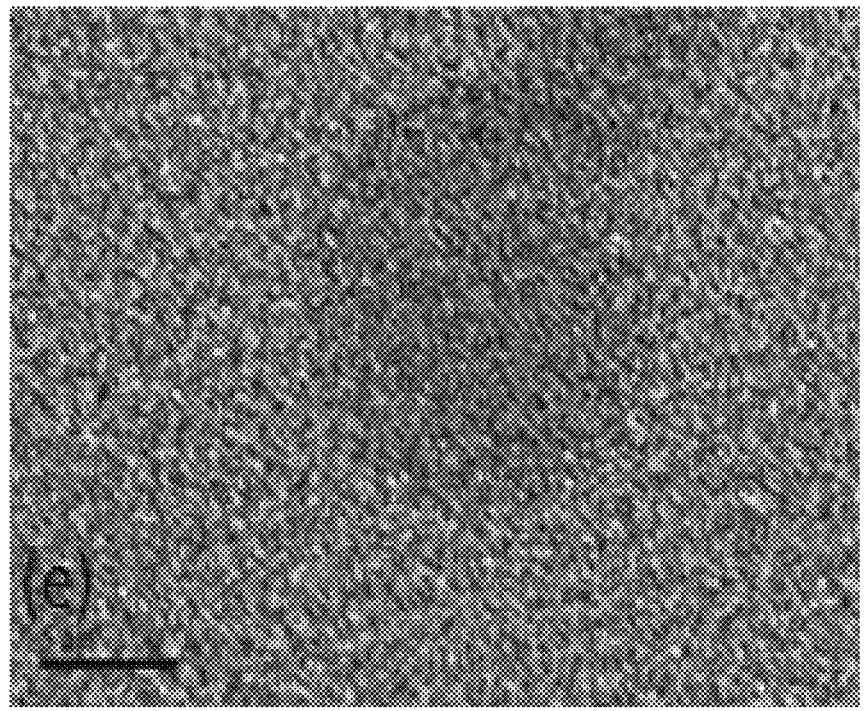
FIG. 5E show a TEM image of an exemplary 30% $CuFe_2O_4$/HYPS specimen on 5 nm scale.
Figure 5F:
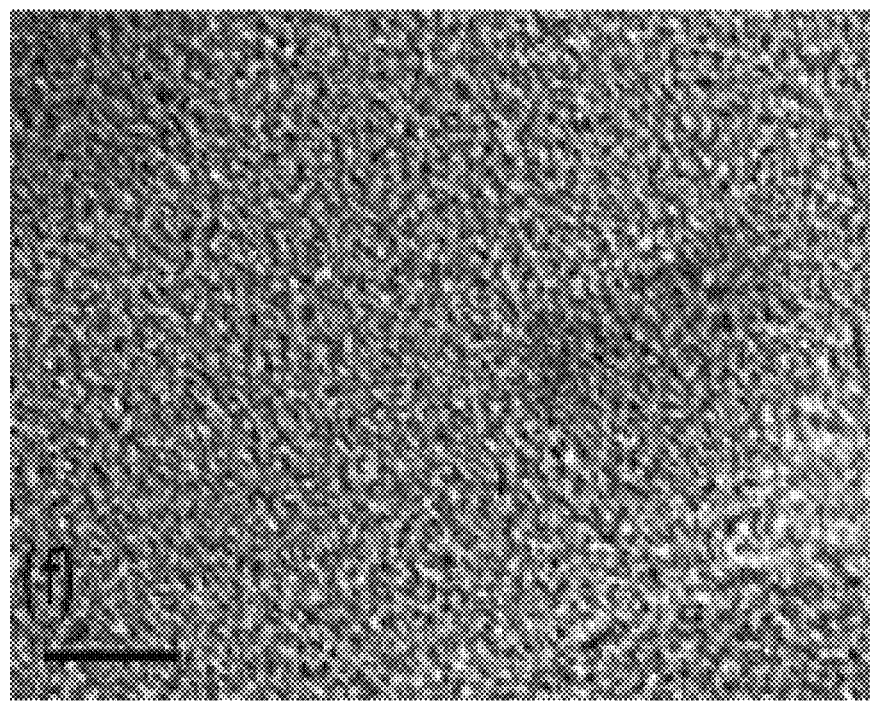
FIG. 5F show a TEM image of an exemplary 30% $CuFe_2O_4$/HYPS specimen on 5 nm scale.

The results of energy dispersive x-ray spectroscopy (EDS) are shown in FIGS. 4G and 4H. The EDS results provide further evidence of the presence of chitosan in the coated 30% $CuFe_2O_4$ on HYPS sample. From the EDS spectra it can be seen that silica is the main element present in the sample, followed by oxygen which derives from both chitosan and silica, and carbon from the chitosan.

FIG. 4I through 4P show the SEM morphological images and corresponding EDS elements dot mappings of a cisplatin-doped, chitosan-coated $CuFe_2O_4$ on HYPS sample. The cisplatin loading is about 30 mg, while chitosan coating can vary between 0.06 to 0.6 wt. %. The presence of different elements was represented in different colors. Based on their concentrations, the elements are specified in brighter region. The mapping distributions of elements clearly shows the coexistence of Cu, Fe, chitosan, and Pt complex along with chloride ligands over HYPS. The elemental distributions evidently show the homogenized distribution of elements over spherical silica.

FIG. 5A to 5F show transmission electron microscope (TEM) images of 30 wt. % $CuFe_2O_4$ on HYPS. The low magnification images, i.e., 200 nm (FIG. 5A) and 100 nm (FIG. 5B), indicate the presence of uniformly distributed silica spheres with particle size of about 80 nm, e.g., at least 50, 55, 60, 62.5, 65, 67.5, 70, 72.5, 75, 77.5, 80, 82.5, or 85 nm and/or up to 125, 120, 115, 110, 105, 100, 97.5, 95, 92.5, 90, 87.5, 85, 82.5, 80, 77.5, or 75 nm. Ferrite based nanoparticles usually form agglomeration to decrease the surface energy. In the exemplary materials, $CuFe_2O_4$ nanoparticles were observed to be dispersed over HYPS. In line with XRD analysis, lattice fringes corresponding to the copper ferrite was confirmed with spacing value of 0.25 nm, e.g., at least 0.18, 0.19, 0.2, 0.21, 0.22, 0.23, 0.24, or 0.25 nm and/or up to 35, 34, 33, 32, 31, 30, 29, 28, 27, 26, or 25 nm. The average particle size ranges between 6 to 12 nm, e.g., at least 3.5, 4, 4.5, 5, 5.5, 5.75, 6, 6.25, or 6.5 nm and/or up to 15, 14.5, 14, 13.75, 13.5, 13.25, 13, 12.75, 12.5, 12.25, 12, 11.75, or 11.5 nm.

Figure 6A:
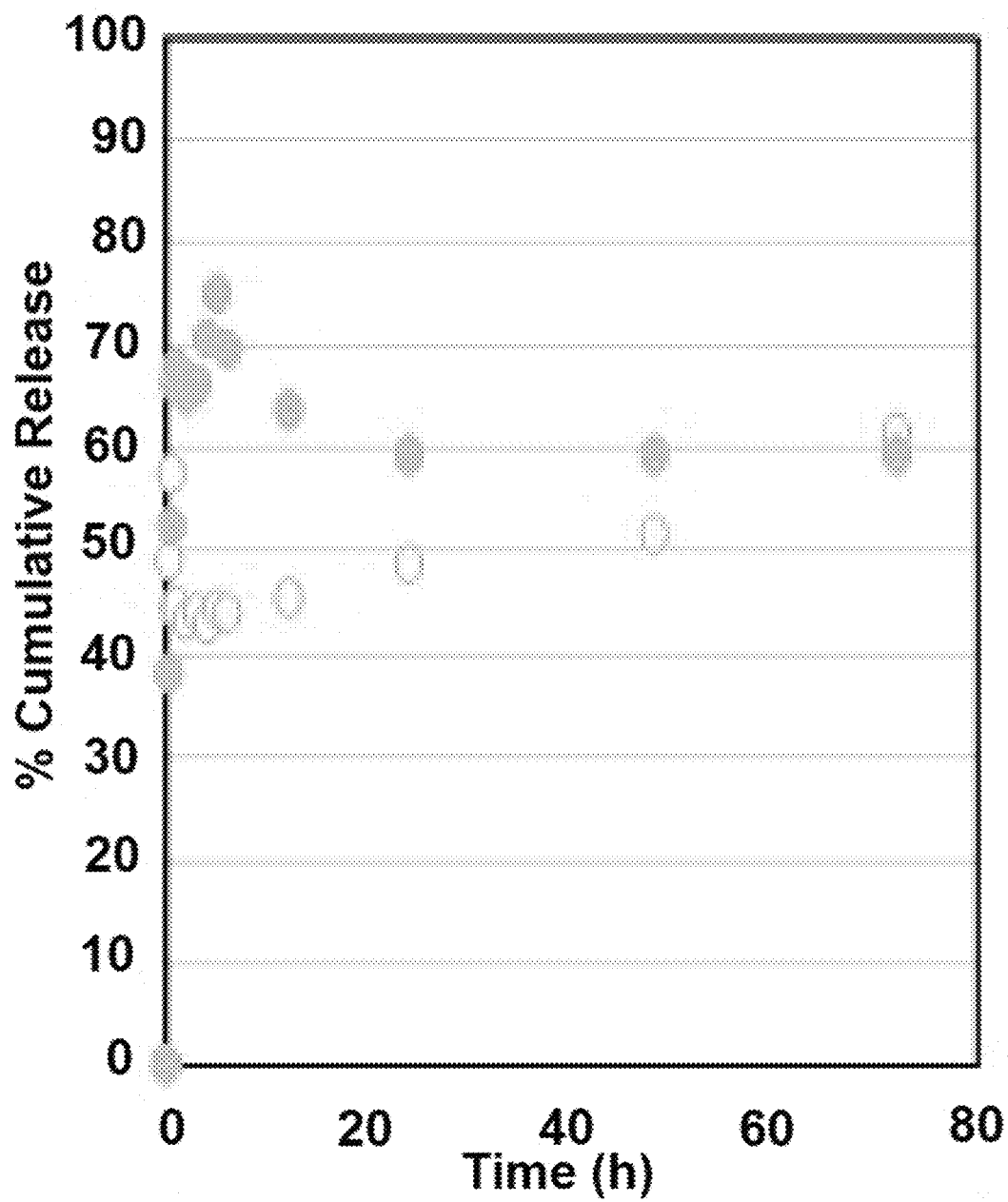
FIG. 6A shows plots of the percentage cumulative cisplatin release in tumor at pH 5 for 24 hours using 30% $NiFe_2O_4$ spinel ferrites with (●) and without (○) chitosan coating.
Figure 6B:
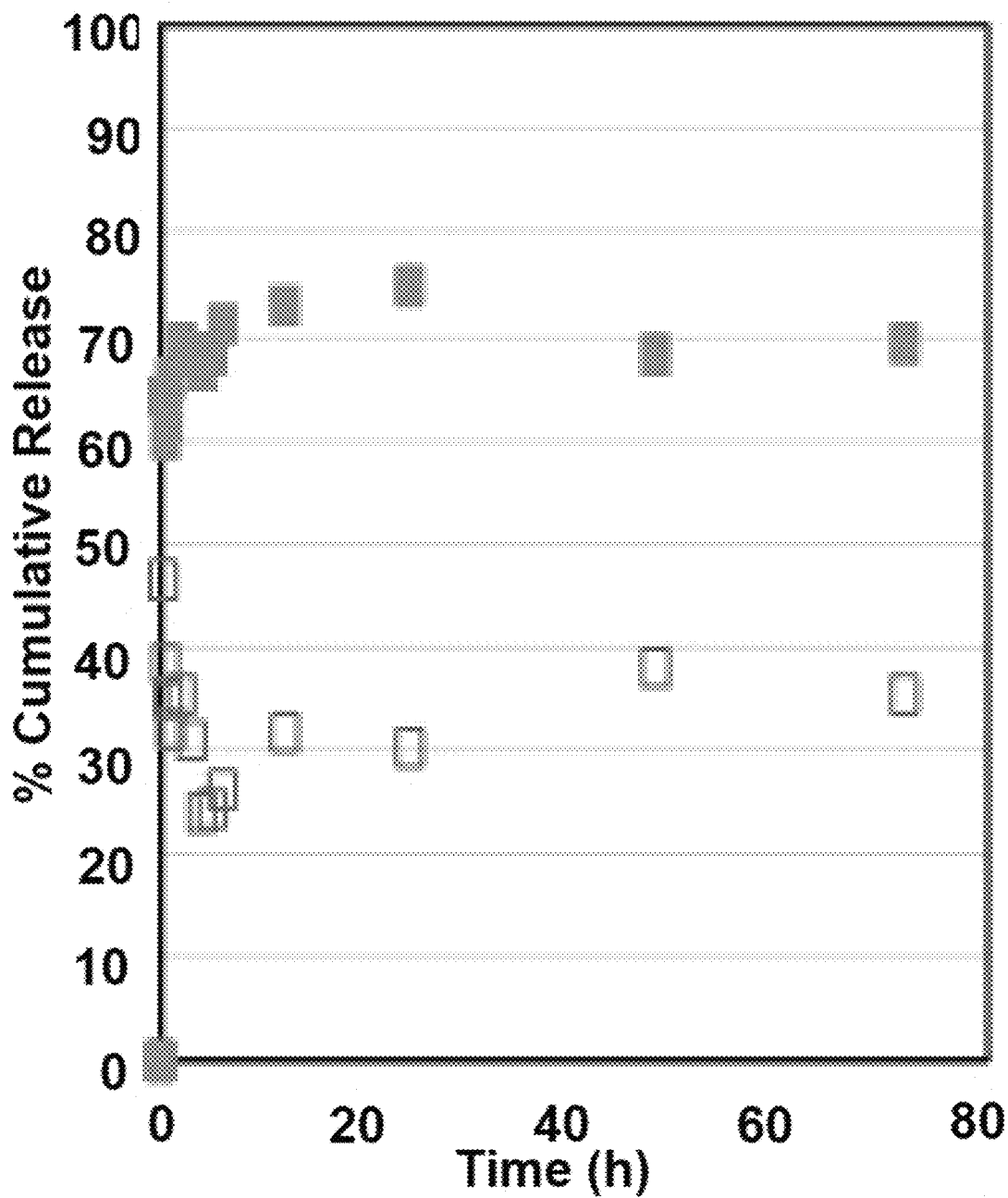
FIG. 6B shows plots of the percentage cumulative cisplatin release in tumor at pH 5 for 24 hours using 30% $MnFe_2O_4$ spinel ferrites with (■) and without (□) chitosan coating.
Figure 6C:
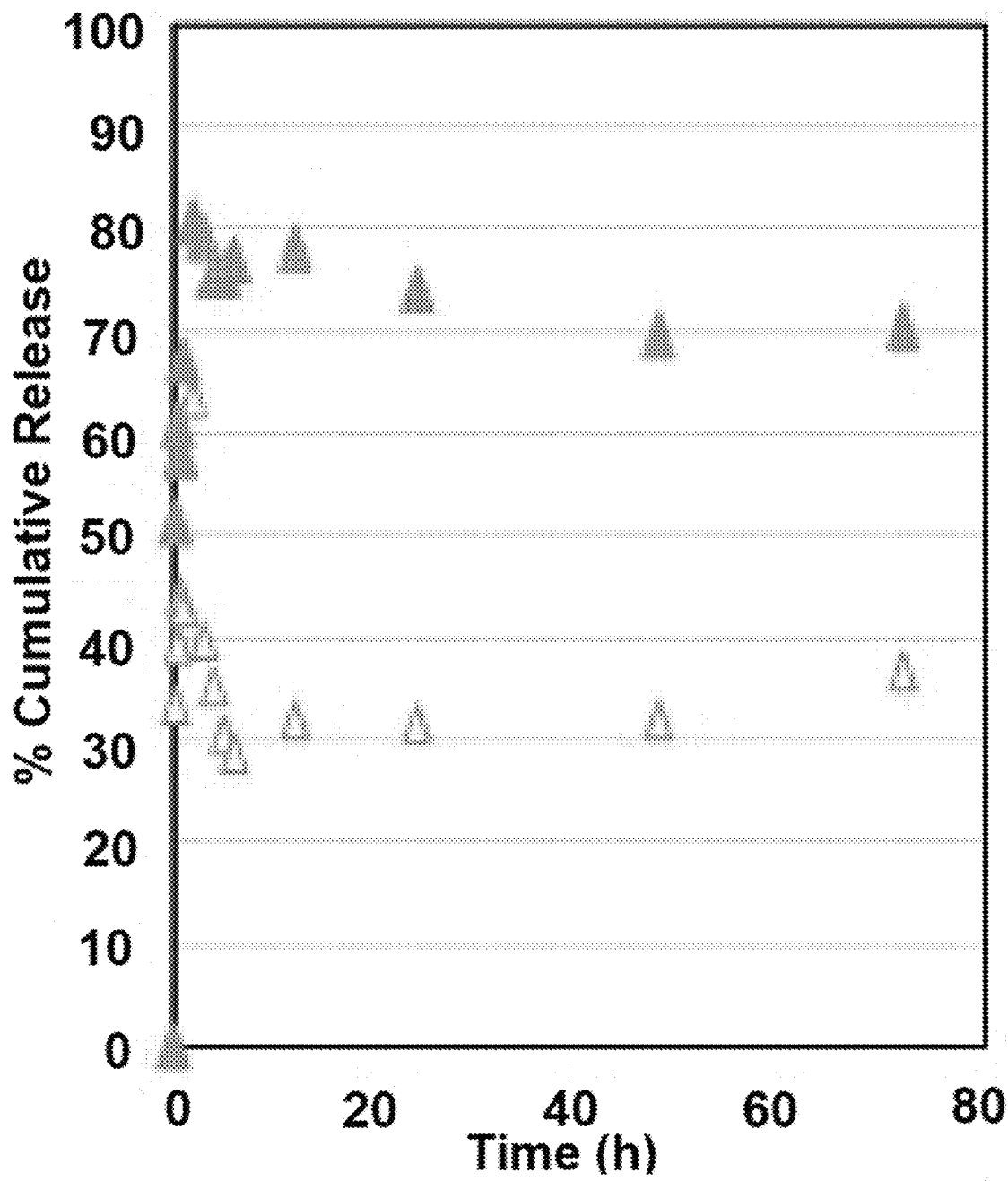
FIG. 6C shows plots of the percentage cumulative cisplatin release in tumor at pH 5 for 24 hours using 30% $CoFe_2O_4$ spinel ferrites with (▲) and without (△) chitosan coating.
Figure 6D:
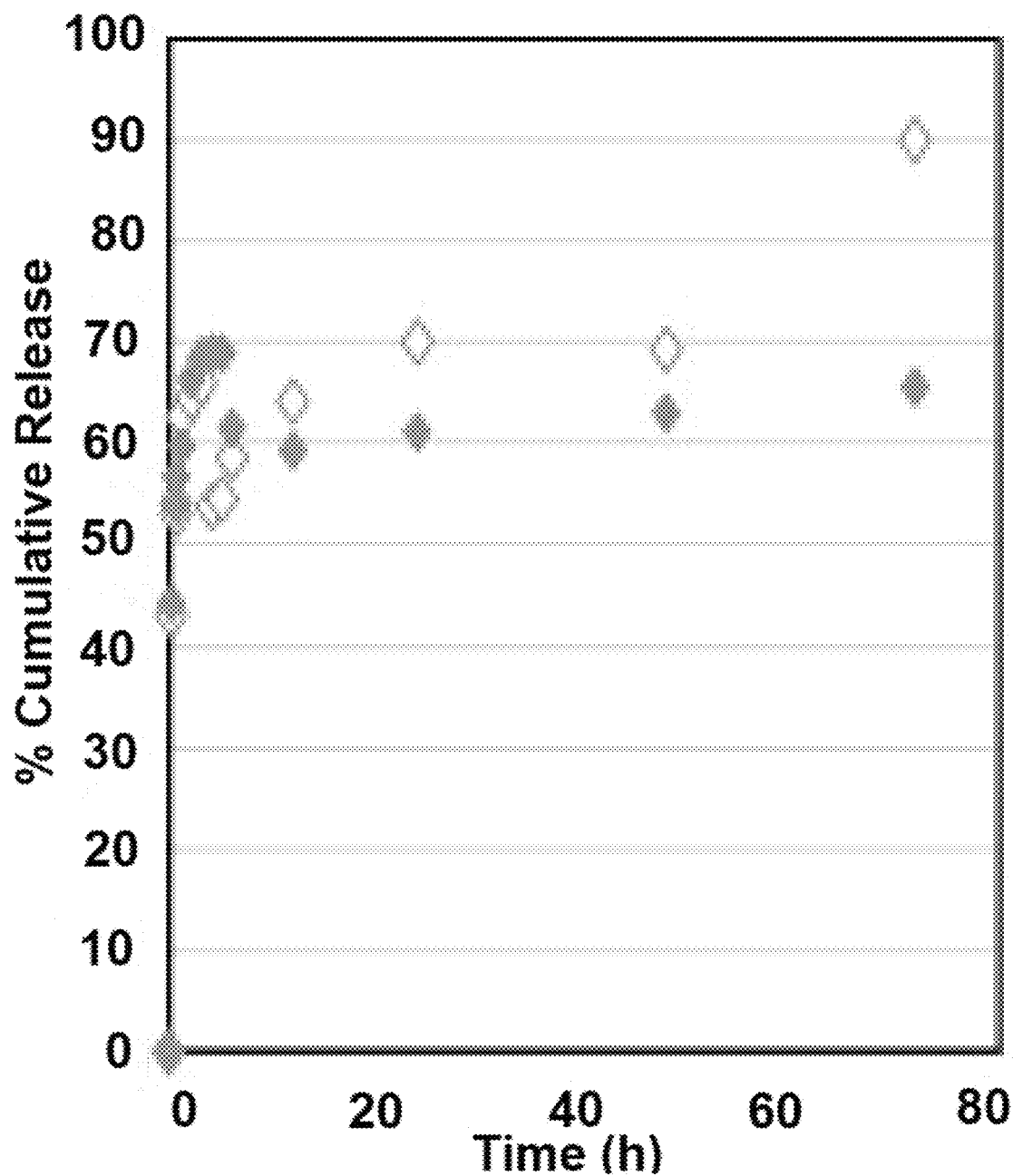
FIG. 6D shows plots of the percentage cumulative cisplatin release in tumor at pH 5 for 24 hours using 30% $CuFe_2O_4$ spinel ferrites with (♦) and without (◇) chitosan coating.

FIG. 6A to 6D shows the drug release of profile of exemplary pinel ferrite-based systems, studied at simulated tumor acid pH conditions (pH 5) and 37° C. for 72 hours. The cisplatin was maintained at 0.15 mmol per gram of spinel HYPS nanosupport. Among the different nanoformulations, the order of cisplatin drug release was: $CuFe_2O_4$ on HYPS (FIG. 6D)>$NiFe_2O_4$ on HYPS (FIG. 6A)>$MnFe_2O_4$ on HYPS (FIG. 6B)~$CoFe_2O_4$ on HYPS (FIG. 6C). The exemplary $CuFe_2O_4$ on HYPS material (FIG. 6D) illustrated the highest percentage cumulative cisplatin release of 90% over 72 hours. After chitosan wrapping, the $CoFe_2O_4$ on HYPS sample (FIG. 6C) showed the highest percentage increase of cisplatin release (70%), while the $NiFe_2O_4$ on HYPS sample (FIG. 6A) showed significant initial burst release. The release experiments in FIG. 6D shows that the fabrication of $CuFe_2O_4$ on HYPS with a chitosan coating does not significantly affect the cisplatin release at acidic tumor condition. The chitosan-coated $MnFe_2O_4$ on HYPS (FIG. 6B) showed initial burst release but remains second-best in drug release over 72 hour (71%). The percentage initial cisplatin burst release for the $CuFe_2O_4$ on HYPS sample was low, i.e., around 10%, which indicates the positive effect of $CuFe_2O_4$ on HYPS with respect to the cisplatin release rate. The trend indicates a synergism between $CuFe_2O_4$, cisplatin and the HYPS structure, which helps to release high percentages of loaded cisplatin, as seen in FIG. 6D. However, cisplatin on Ni and Mn-based spinel ferrite showed an initial burst release of about 90% at about 30 min, which then reduces to 60 to 70% at 72 hours. This indicates that apart from the $CuFe_2O_4$ on HYPS sample, the exemplary $CoFe_2O_4$ and $MnFe_2O_4$ formulations may be the other potential nanocarriers for drug delivery applications.

In Vitro Anti-Cancer Study

Cisplatin is a potent chemotherapeutic drug that prevents cell division. However, cisplatin has multi-organ off target toxicity, mainly in the kidneys, liver, heart, nerves, and ears. To reduce these side effects and to ensure specific tumor targeting, cisplatin-loaded, chitosan-coated $CuFe_2O_4$ on HYPS nanoparticles may limit or prevent the drug from being prematurely cleared from circulation, while the $CuFe_2O_4$ coating can allow targeted delivery of these nanoparticles to prevent off target effects.

Figure 7:
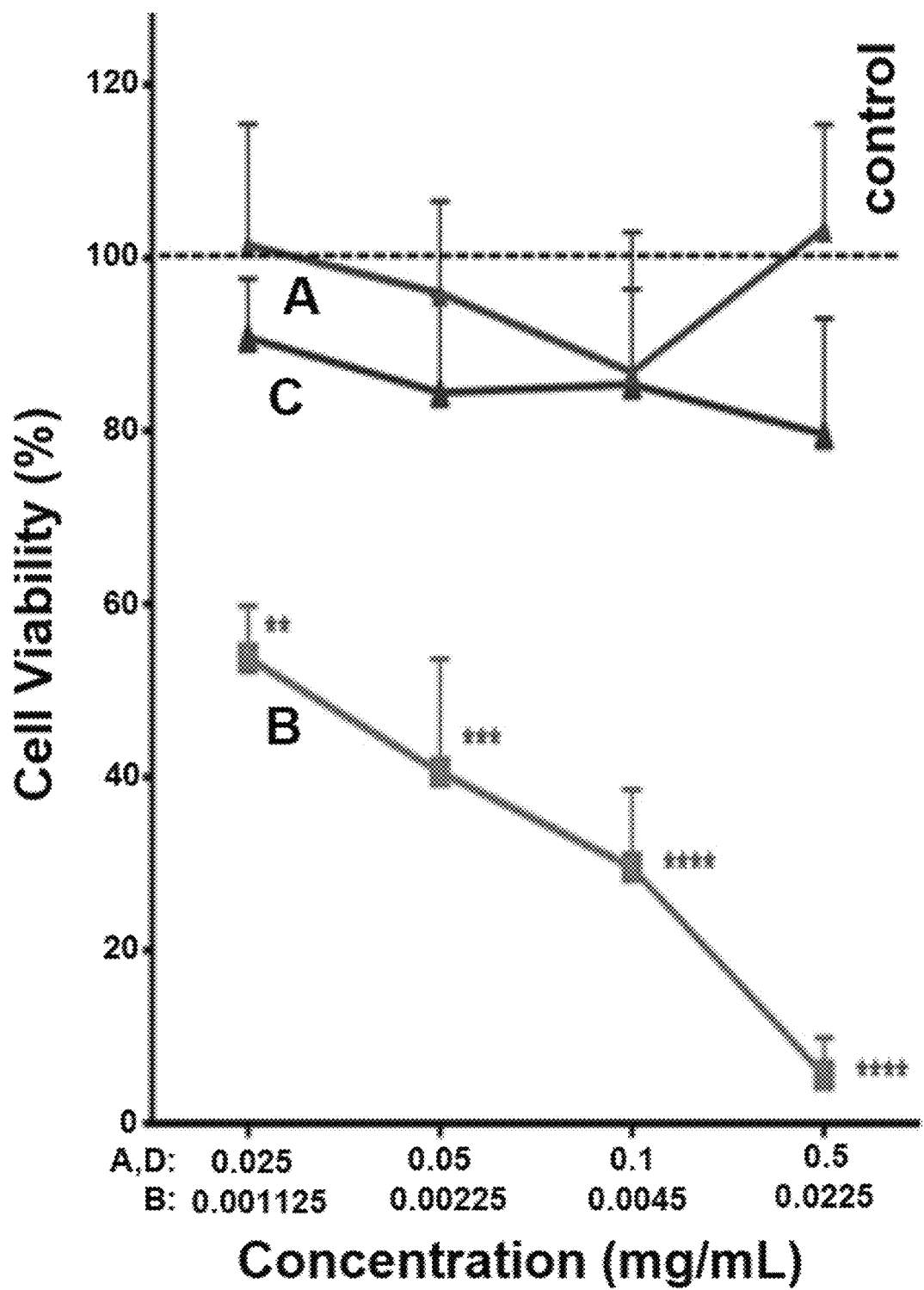
FIG. 7 shows plots of the percentage cell viability using MTT 3-(4,5-dimethylthiazol-2-yl)-2,5-diphenyltetrazolium (MTT) assay on the MCF7 cell line for 48 hours with Group A ($CuFe_2O_4$ on HYPS silica), Group B (cisplatin), and group C (cisplatin-loaded, chitosan-coated $CuFe_2O_4$ on HYPS silica)

To investigate the cytotoxic efficiency of chitosan-coated $CuFe_2O_4$ on HYPS, cell viability was assessed using the MTT assay. In the MTT assay, healthy cells are able to reduce MTT to the purple-colored formazan crystals, while unhealthy/dead cells cannot. In order to determine preferred release rates, a chitosan-coating of cisplatin-doped $CuFe_2O_4$ on HYPS nanoformulation was performed as described in Method I, above. MCF7 cells were treated with the following conditions: Group A ($CuFe_2O_4$ on HYPS silica), Group B (cisplatin alone), chitosan-coated, cisplatin-loaded $CuFe_2O_4$ on HYPS (Group C) as shown in FIG. 7. Chitosan-coated, cisplatin-doped $CuFe_2O_4$ on HYPS (Group C) did not result is any noticeable reduction in cell viability.

Therefore, a slight modification in chitosan coating was performed, i.e., coating the $CuFe_2O_4$ on HYPS support before the cisplatin loading, then performing the cisplatin loading or doping on a chitosan-coated chitosan-coated $CuFe_2O_4$ on HYPS support. A pH assisted chitosan coating was carried out over spinel ferrite on HYPS in a first step, followed by loading of cisplatin in a subsequent step, as described for Method II, above.

FIG. 8 shows the percentage cell viability using the MTT assay on the MCF7 and HEK293 cell lines. As seen in FIG. 8, this route showed surprisingly promising anticancer activity. MCF7 and HEK293 cells were treated for 48 hours with: Group A ($CuFe_2O_4$ on HYPS silica), Group B (cisplatin alone), cisplatin loaded onto uncoated $CuFe_2O_4$ on HYPS (Group D), and cisplatin loaded onto chitosan-coated $CuFe_2O_4$ on HYPS (Group E). For Groups A, D, and E, treatment concentrations were as follows: 0.025, 0.05, 0.1, and 0.5 mg/mL. To accurately reflect the concentration of cisplatin (Group B) that is encapsulated within these nanoparticles, drug loading experiments were used. Therefore, Group B treatment concentrations were halved, i.e., 0.001125, 0.00225, 0.0045, and 0.0225 mg/mL. The combination of $CuFe_2O_4$ and silica (Group A) did not have a significant effect on cell viability. The pure cisplatin (Group B) and the cisplatin-loaded nanoparticles (groups D and E) caused a reduction in cell viability on both HEK293 and MCF7. The effect on the breast cancer cell line, MCF7, was more pronounced than in the human embryonic kidney cell line, HEK293. At the lowest tested concentration for cisplatin (Group B), cisplatin-loaded $CuFe_2O_4$ on HYPS (Group D), and cisplatin-loaded, chitosan-coated $CuFe_2O_4$ on HYPS silica by Method II (Group E), cell viability of MCF7 was 58.17% (B), 63.36% (D), and 70.73% (E), respectively. However, in HEK293, it was 73.47% (B), 80.24% (D), and 95.07% (E), respectively. Cisplatin and cisplatin-loaded nanoparticles (Groups D and E) showed a dose dependent increase in cytotoxicity in both MCF7 and HEK293.

For plot A, the MTT assay on the MCF7 cell line using the nanoformulation of cisplatin on uncoated cisplatin-doped $CuFe_2O_4$ on HYPS (Group D), with 4 independent experiments. Plots B and C show the MTT assay on the MCF7 and HEK293 cell lines using prepared by Method II (Group E), n=5 independent experiments. The dashed line represents an untreated control, and the error bars represent±standard error of the mean (SEM), while the indicators $p<0.01$; * $p<0.001$; **** $p<0.0001$ versus control using two-way ANOVA with Dunnett's multiple comparisons post hoc test.

Figure 8A:
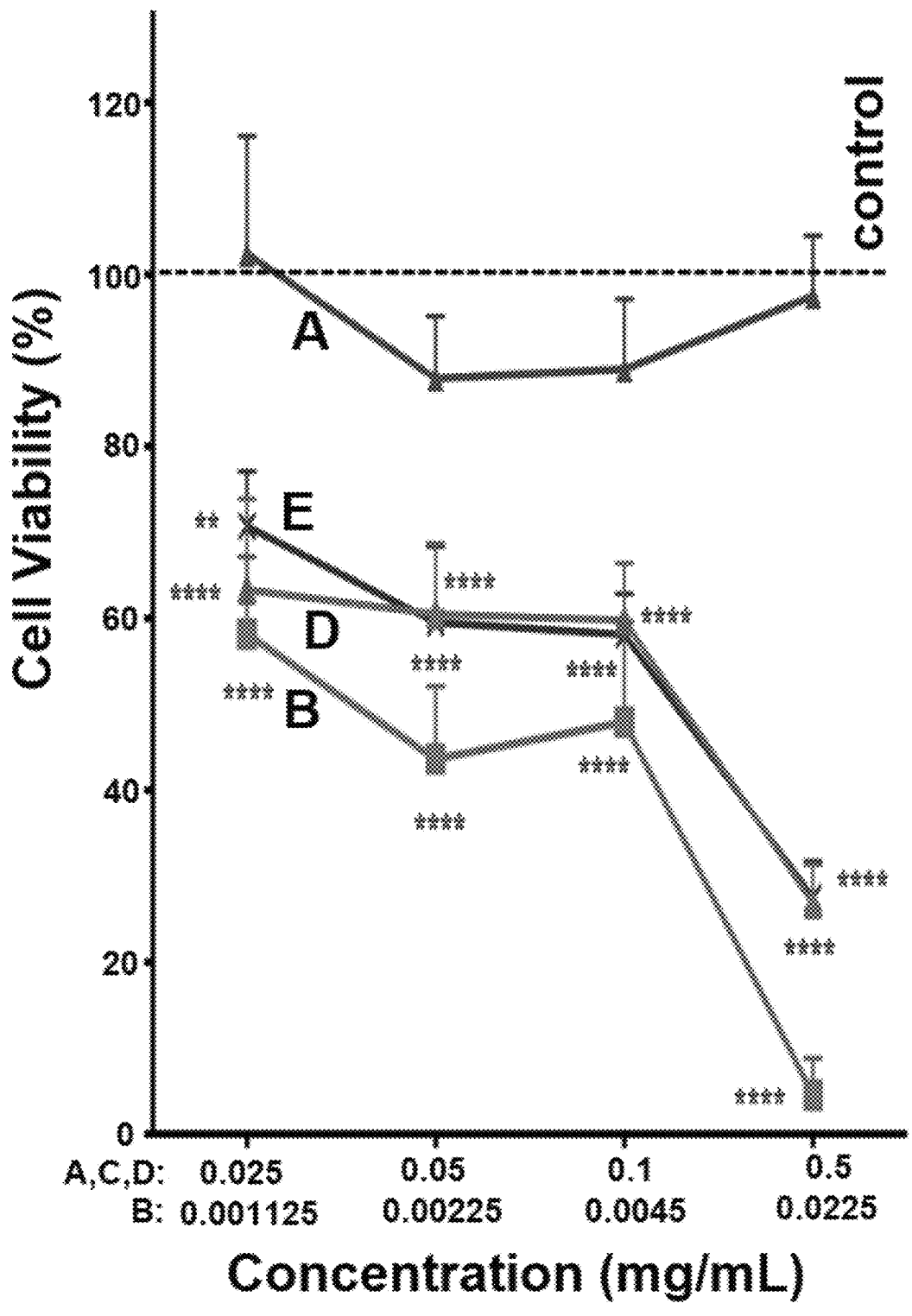
FIG. 8A shows plots of the percentage cell viability using the MTT assay on the MCF7 cell line.
Figure 8B:
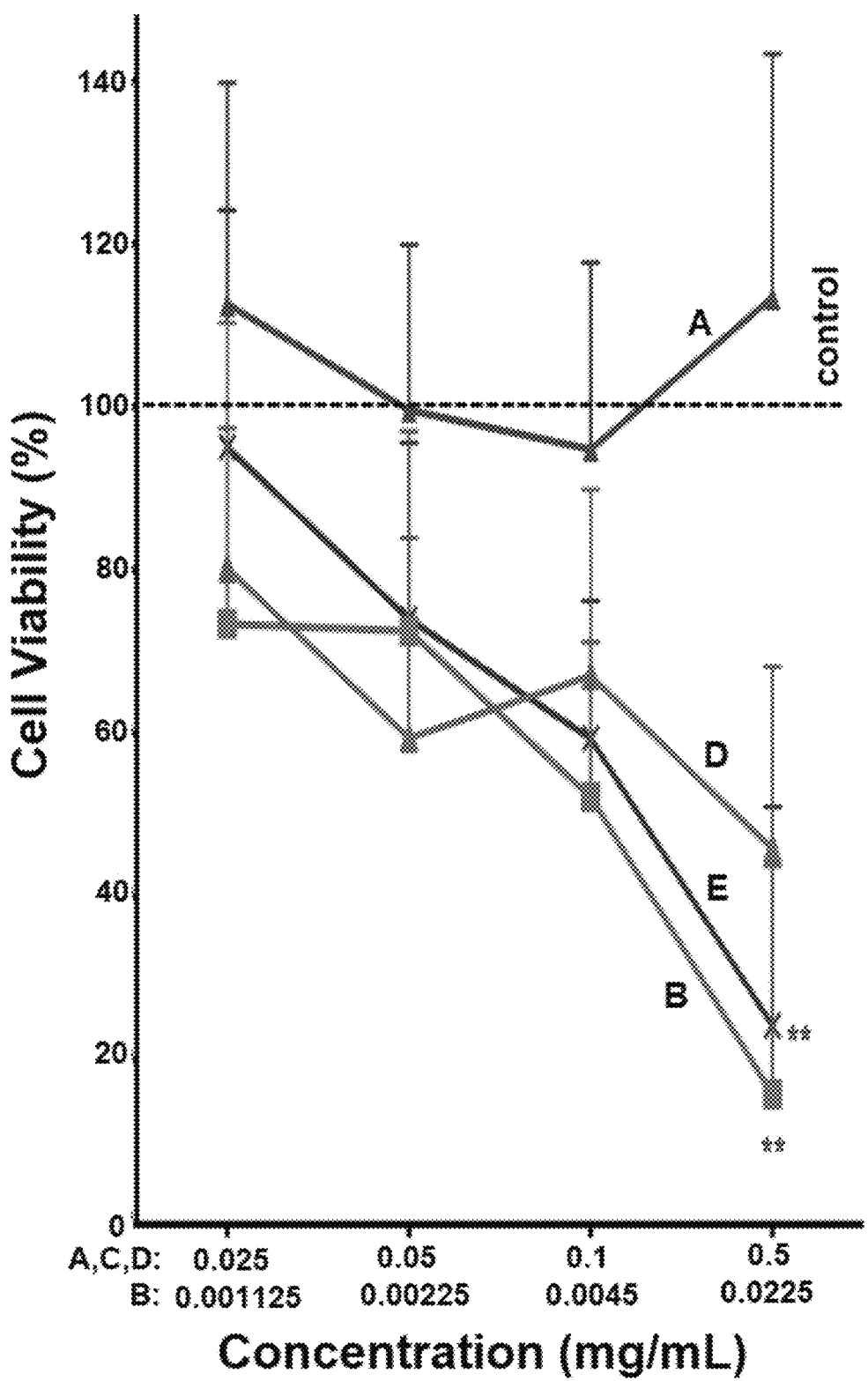
FIG. 8B shows plots of the percentage cell viability using the MTT assay on the HEK293 cell line.
Figure 9A:
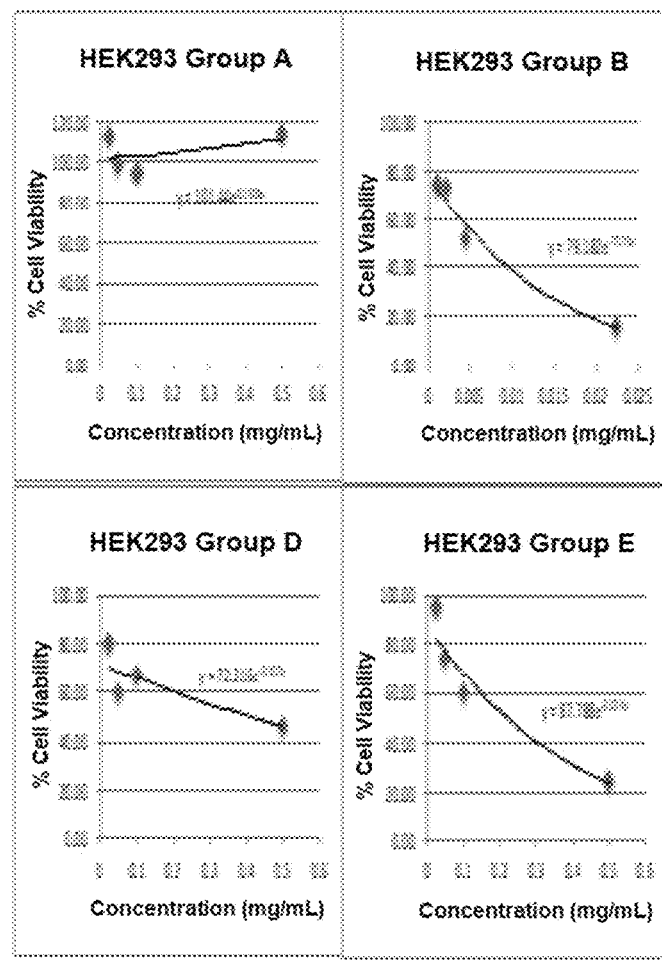
FIG. 9A shows EC50 values using data sets from FIG. 1 to extrapolate the line equation of each condition: Group A ($CuFe_2O_4$ on HYPS silica), Group B (cisplatin), Group C (cisplatin-loaded, chitosan-coated $CuFe_2O_4$ on HYPS silica, made by Method I, described below), and Group E (chitosan-coated, cisplatin-loaded $CuFe_2O_4$ on HYPS silica, made by Method II, described below) on the HEK293 cell line.
Figure 9B:
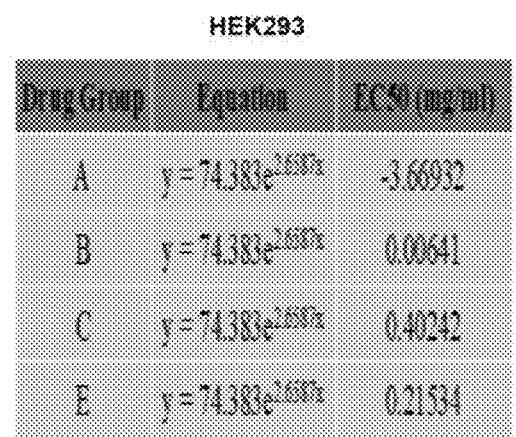
FIG. 9B shows EC50 values from the line equations calculate each drug group on the HEK293 cell line.
Figure 9C:
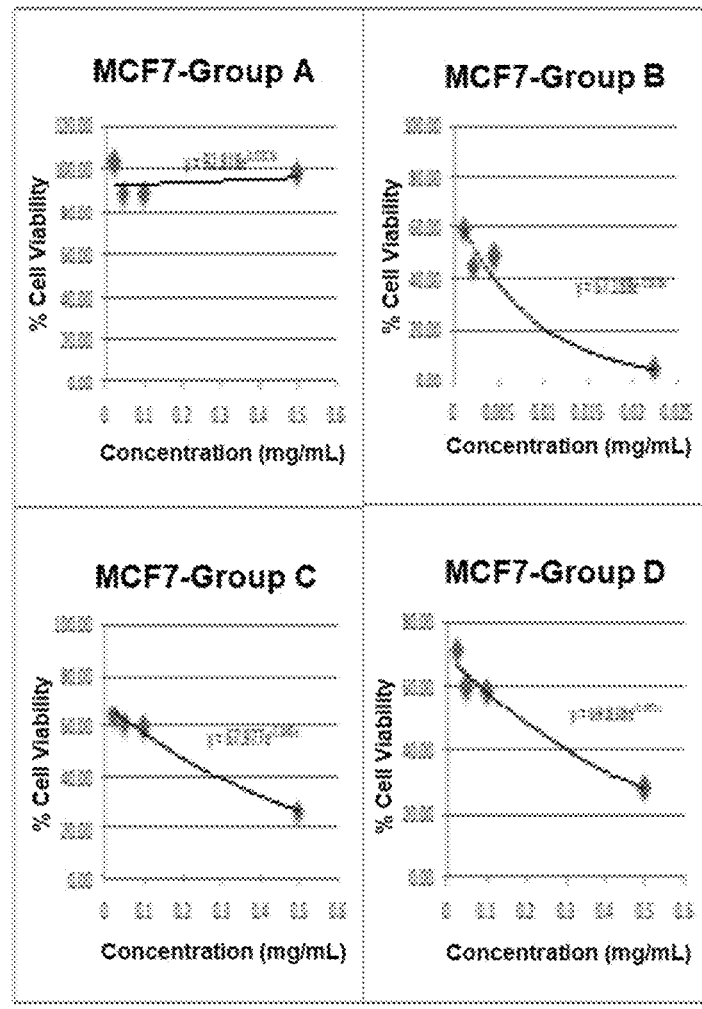
FIG. 9C shows EC50 values using data sets from FIG. 1 to extrapolate the line equation of each condition: Group A ($CuFe_2O_4$ on HYPS silica), Group B (cisplatin), Group C (cisplatin-loaded, chitosan-coated $CuFe_2O_4$ on HYPS silica, made by Method I, described below), and Group E (chitosan-coated, cisplatin-loaded $CuFe_2O_4$ on HYPS silica, made by Method II, described below) on the MCF7 cell line.
Figure 9D:
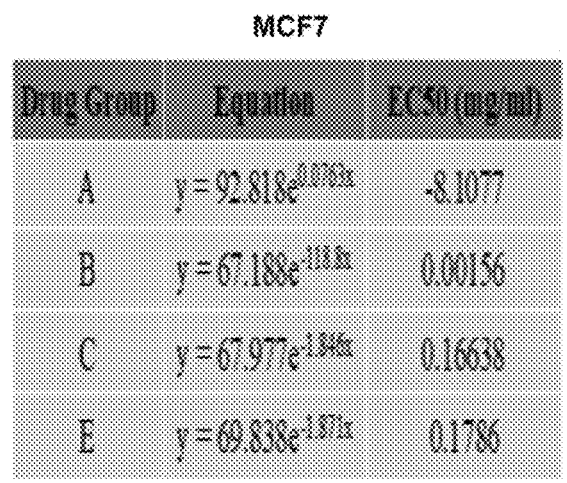
FIG. 9D shows EC50 values from the line equations calculate each drug group on the MCF7 cell line.

FIG. 9A to 9D shows the half maximum effective concentration ($EC_{50}$) calculated from the line equation of each condition. These results show that the chitosan-coated cisplatin-loaded $CuFe_2O_4$ on HYPS nanoparticles can effectively reduce the cell viability of both MCF7 and HEK293 with a similar efficiency to the pure cisplatin. Accordingly, the inventive nanoparticles are useful for drug delivery. FIGS. 9A and 9C show data sets extrapolated from FIG. 1 using a linear equation of each condition, with Group A being $CuFe_2O_4$ on HYPS, Group B being pure cisplatin, Group C being chitosan-coated, cisplatin-doped $CuFe_2O_4$ on HYPS silica (Method I), and Group E being chitosan-coated, cisplatin-doped $CuFe_2O_4$ on HYPS silica (Method II) on the HEK293 cell line (FIG. 8A) and the MCF7 cell line (FIG. 8C). FIGS. 8B and 8D show linear fitting equations to calculate the $EC_{50}$ for each drug group on the HEK293 and MCF7 cell lines.

FIG. 10 shows a schematic representation of methods of making and using inventive nanocomposites as described above, beginning with monodisperse hydrophilic spherical HYPS silica, adding a desired metal-ferrite, and coating with chitosan then loading with cisplatin or loading cisplatin and coating with cisplatin, followed by presentation to one or more cancerous cell lines.

Figure 11:
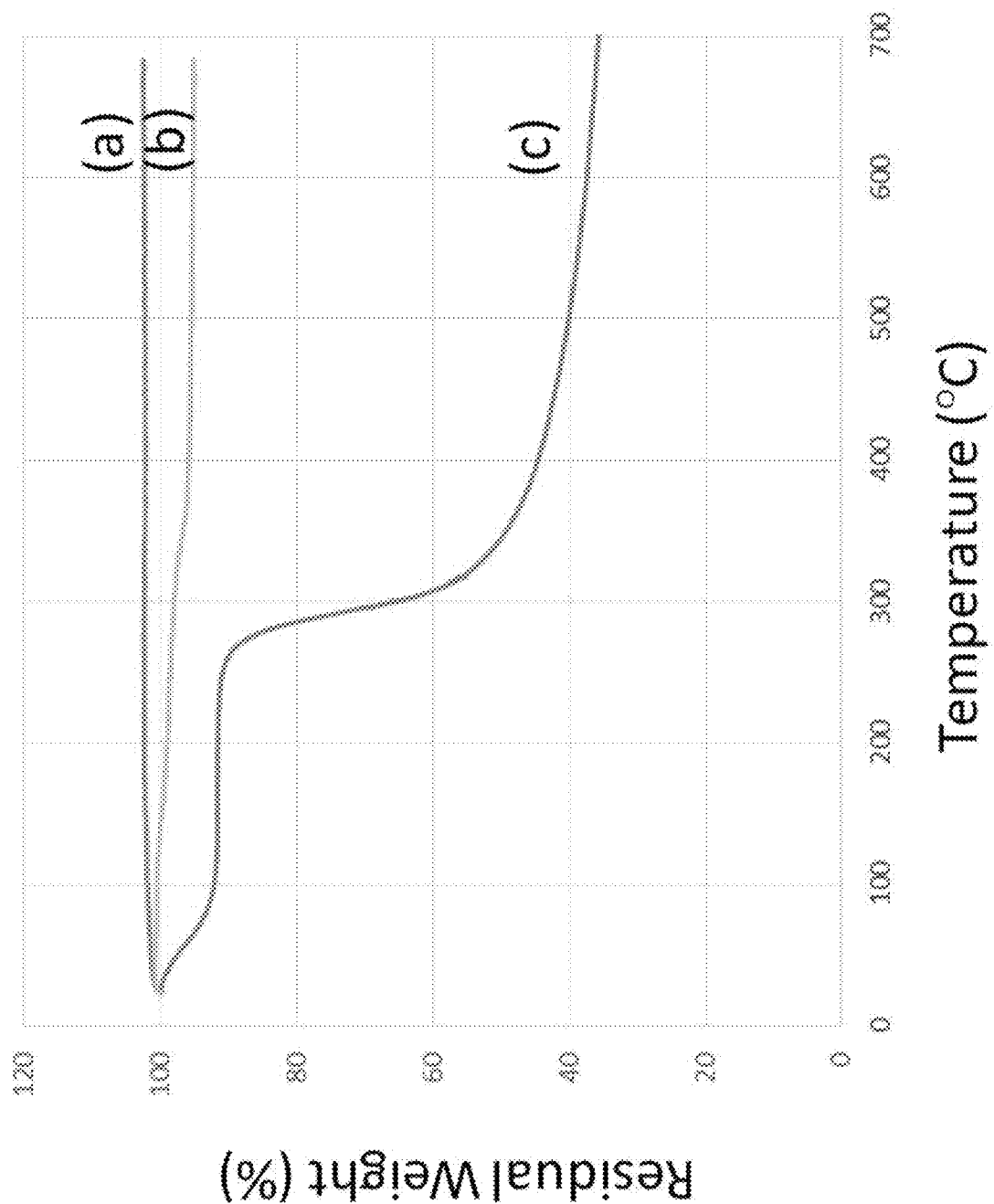
FIG. 11 shows TGA thermograms of 30% $CuFe_2O_4$ on HYPS (a), 0.6% (w/v) chitosan coated 30% $CuFe_2O_4$/HYPS (b), and chitosan (c)

FIG. 11 shows a further thermogravimetric analysis (TGA) plot of the support (a), a lesser-coated chitosan-coated support (b), and pure chitosan (c). The thermogram of 30% $CuFe_2O_4$ on HYPS shown in FIG. 11 (plot "a") indicates that the material is thermally stable for the temperature range analyzed. However, the chitosan-coated sample in FIG. 11 (plot "b") showed slight degradation with the rise in temperature. The weight loss observed in the case of chitosan-coated 30% $CuFe_2O_4$/HYPS was attributed to the pyrolysis of the chitosan coated on the support. The exemplary chitosan thermogram shown in FIG. 11 (plot "c") showed a two step degradation profile, i.e., a first weigh loss regime from 120 to 260° C. and a second weight loss regime from 300 to 400° C. The final residue content of the lesser chitosan-coated sample was 95.2%.

Figure 12:
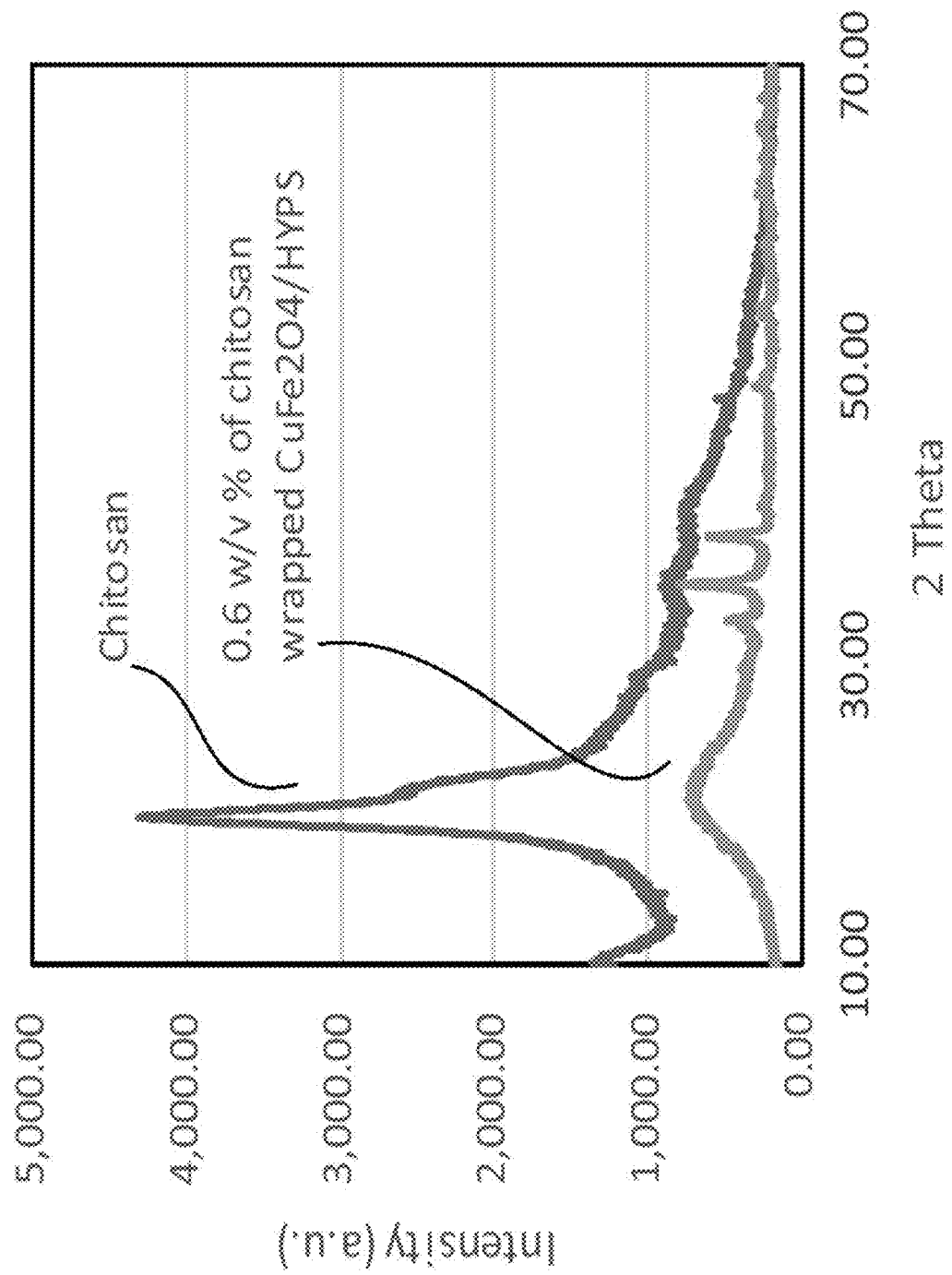
FIG. 12 shows XRD patterns of chitosan and chitosan-coated 30 wt. % $CuFe_2O_4$ on HYPS silica.

FIG. 12 shows an XRD pattern of greater chitosan-coated 30% $CuFe_2O_4$/HYPS sample along with plain chitosan. A slight increase in the intensity of the amorphous curve at the 2θ angle of 22.5° was observed for the chitosan coated sample.

Numerous modifications and variations of the present invention are possible in light of the above teachings. It is therefore to be understood that within the scope of the appended claims, the invention may be practiced otherwise than as specifically described herein.

The invention claimed is:

1. A composition in the form of composite particles, comprising:
    spherical hybrid plasma sprayed silica (HYPS) particles as a first part of a carrier;
    a metal ferrite of formula $CuFe_2O_4$ as a second part of the carrier;
    a coating comprising at least 75 wt. %, based on the total weight of the coating, of chitosan; and
    cisplatin, disposed within and/or on at least one of the carrier and the coating,
    wherein the composition is in the form of irregular spheroidal composite particles,
    wherein Cu is present in the metal ferrite in an amount of 15 to 45 wt. %, based on the total weight of the metal ferrite,
    wherein the carrier is porous having a pore volume in a range from 0.15 to 0.25 $cm^3/g$,
    wherein the metal ferrite is attached onto the surface of the HYPS particles,
    wherein the HYPS particles and the metal ferrite form at least 75 wt. % of the carrier, based on total carrier weight,
    wherein the carrier is a core of the composite particles and the carrier is in direct contact with the coating, and the coating is an outermost layer of the composite particles,
    wherein the coating is directly attached to the carrier through hydrogen bonding, and
    wherein the composition releases 90 wt. % of the cisplatin within 72 hours, at a pH of 5.5, and a temperature of 37 C.

2. The composition of claim 1, wherein the HYPS particles have an average diameter of from 50 to 100 nm, and wherein a distribution of the HYPS particles is monomodal.

3. The composition of claim 1, wherein metal ferrite is in the form of particles having an average particle size in a range of from 4 to 15 nm.

4. The composition of claim 1, wherein the chitosan in the coating has a Mw in a range of from 30 to 250 kDa.

5. The composition of claim 1, wherein the coating constitutes no more than 20 wt. % of the total weight of the composition.

6. The composition of claim 1, wherein the carrier comprises at least 95 wt. % of the metal ferrite and the HYPS particles, based on the total weight of the carrier.

7. The composition of claim 1, wherein the cisplatin is present, in mmol per gram of the composition, in a range of from 0.05 to 0.25.

8. The composition of claim 1, wherein the carrier has a saturation magnetization in a range of from 2.5 to 12.5 emu/g.

9. The composition of claim 1, wherein the metal ferrite is present in the carrier, relative to the total weight of the carrier, in an amount of from 15 to 40 wt. %.

10. The composition of claim 1, wherein at least 25 wt. % of the cisplatin is present in the coating.

11. The composition of claim 1, wherein the carrier, the coating, and the cisplatin are at least 85 wt. % of the total weight of the composition.

* * * * *